Figure 3:
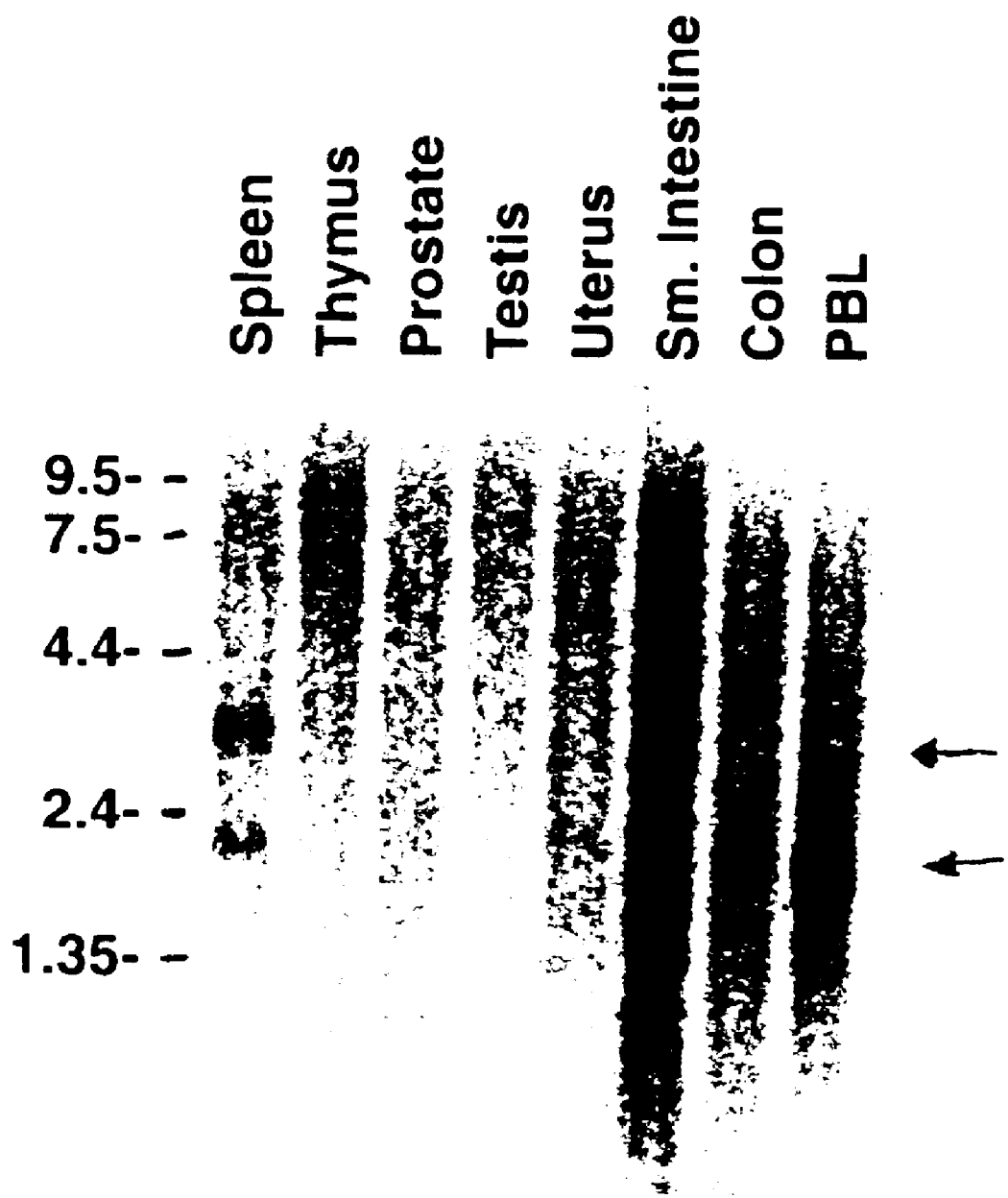

United States Patent [19]
Xu et al.

[11] Patent Number: 6,013,479
[45] Date of Patent: Jan. 11, 2000

[54] HUMAN EMR1-LIKE G PROTEIN COUPLED RECEPTOR

[75] Inventors: Hong Xu, Mystic; Victoria L. Cohan, East Lyme, both of Conn.; Susan G. Stuart, Montara, Calif.

[73] Assignee: Incyte Pharmaceuticals, Inc., Palo Alto, Calif.

[21] Appl. No.: 09/110,116

[22] Filed: Jul. 2, 1998

[51] Int. Cl.$^7$ .......................... C07H 21/04; C12N 15/02; C12N 15/63
[52] U.S. Cl. .................. 435/69.1; 536/23.1; 536/24.31; 435/320.1; 435/325; 435/252.3; 435/172.3
[58] Field of Search .............................. 536/23.1, 24.31; 435/320.1, 325, 252.3, 172.3, 69.1; 530/350

[56] References Cited

PUBLICATIONS

PROSITE: PS00237.
Watson, S. And Arkinstall, S., *The G–Protein Linked Receptor FactsBook*, Academic Press, San Diego, CA, pp. 2–6 (1994).
Baud, V., et al., "EMR1, an Unusual Member in the Family of Hormone Receptors with Seven Transmembrane Segments," *Genomics*, 26:334–344 (1995) (GI 784993).
Gray, JX, et al., "CD97 is a Processed, Seven–Transmembrane, Heterodimeric Receptor Associated with Inflammation,," *Journal of Immunology*, 157(12):5438–5447 (1996).
Baud, V., et al., (GI 784993) GenBank Sequence Database (Accession X81479), National Center for Biotechnology Information, National Library of Medicine, Bethesda, Maryland 20894.
Lamerdin, J.E., et al. (GI 2935596) GenBank Sequence Database (Accession AC004262), National Center for Biotechnology Information, National Library of Medicine, Bethesda, Maryland 20894.
Bolton, A.E. and Hunter, W.M., "The Labelling of Proteins to High Specific Radioactivities by Conjugation to a $^{125}$I–Containing Acylating Agent," *Biochem. J.*, 133:529–539 (1973).

*Primary Examiner*—Lila Feisee
*Assistant Examiner*—Nirmal S. Basi
*Attorney, Agent, or Firm*—Incyte Pharmaceuticals, Inc.; Colette C. Muenzen

[57] ABSTRACT

The invention provides a human Emr1-like G protein coupled receptor (EGPCR) and polynucleotides which identify and encode EGPCR. The invention also provides expression vectors, host cells, antibodies, agonists, and antagonists. The invention also provides methods for diagnosing, treating or preventing disorders associated with expression of EGPCR.

7 Claims, 16 Drawing Sheets

```
5' GCG TGG GAT ACC CGT ACA GAA ACA ATG CAG GGA CCA TTG CTT CTT CCA GGC CTC
                                                                         54
                         9          18          27          36       45
                                    M   Q   G   P   L   L   L   P   G   L

TGC TTT CTG CTG AGC CTC TTT GGA GCT GTG ACT CAG AAA ACC AAA ACT TCC TGT
 C   F   L   L   S   L   F   G   A   V   T   Q   K   T   K   T   S   C   108
         63          72          81          90          99

GCT AAG TGC CCC CCA AAT GCT TCC TGT GTC AAT ACT CAC TGC ACC TGC AAC
 A   K   C   P   P   N   A   S   C   V   N   T   H   C   T   C   N   162
        117         126         135         144         153

CAT GGA TAT ACT TCT GGA TCT GGG CAG AAA CTA TTC CCC TTG GAG ACA
 H   G   Y   T   S   G   S   G   Q   K   L   F   P   L   E   T   216
        171         180         189         198         207

TGT AAC GAC ATT AAT GAA TGT ACA CCA CCC TAT AGT GTA TAT TGT GGA TTT AAC
 C   N   D   I   N   E   C   T   P   P   Y   S   V   Y   C   G   F   N   270
        225         234         243         252         261

TGT GTA TGT TAC AAT GTC GAA GGA GAG AGT TTC TAC TGT CAA TGT CCA GGA TAT
 A   V   C   Y   N   V   E   G   E   S   F   Y   C   Q   C   P   G   Y   324
        279         288         297         306         315

GCT GTA CAT CTG TCT GGG AAT GAA CAA TTC AGT AAT TCC AAT GAG AAC ACC TGT CAG
 R   L   H   S   G   N   E   Q   F   S   N   S   N   E   N   T   C   Q   378
        333         342         351         360         369
```

FIGURE 1A

```
     387         396         405         414         423         432
GAC ACC TCC TCA AAG ACA ACC CAG GGC AGG AAA GAG CTG CAA AAG ATT GTG
 D   T   S   S   K   T   T   Q   G   R   K   E   L   Q   K   I   V 441         450         459         468         477         486
GAC AAA TTT GAG TCA CTT CTC ACC AAT CAG ACT TTA TGG AGA ACA GAA GGG AGA
 D   K   F   E   S   L   L   T   N   Q   T   L   W   R   T   E   G   R 495         504         513         522         531         540
CAA GAA ATC TCA ACA GCT ACC ACT ATT CTC CGG GAT GTG GAA TCG AAA GTT
 Q   E   I   S   T   A   T   T   I   L   R   D   V   E   S   K   V 549         558         567         576         585         594
CTA ACT GCC TTG AAA GAT CCA GAA CAA AAA GTC CTG AAA ATC CAA AAC GAT
 L   T   A   L   K   D   P   E   Q   K   V   L   K   I   Q   N   D 603         612         621         630         639         648
AGT GTA GCT ATT GAA ACT CAA GCG ATT ACA GAC AAT TGC TCT GAA GAA AGA AAG
 S   V   A   I   E   T   Q   A   I   T   D   N   C   S   E   E   R   K 657         666         675         684         693         702
ACA TTC AAC TTG AAC GTC CAA ATG AAC TCA ATG GAC ATC CGT TGC AGT GAC ATC
 T   F   N   L   N   V   Q   M   N   S   M   D   I   R   C   S   D   I 711         720         729         738         747         756
ATC CAG GGA GAC ACA CAA GGT CCC AGT GTC ATT GCC TTT ATC TCA TAT TCT TCT
 I   Q   G   D   T   Q   G   P   S   V   I   A   F   I   S   Y   S   S
```

FIGURE 1B

```
      765            774            783            792            801            810
CTT GGA AAC ATC ATA AAT GCA ACT TTT GAA GAG ATG GAT AAG AAA GAT CAA
 L   G   N   I   I   N   A   T   F   E   E   M   D   K   K   D   Q 819            828            837            846            855            864
GTG TAT CTG AAC TCT CAG GTT GTG AGT GCT GCT ATT GGA CCC AAA AGG AAC GTG
 V   Y   L   N   S   Q   V   V   S   A   A   I   G   P   K   R   N   V 873            882            891            900            909            918
TCT CTC TCC AAG TCT GTG ACG CTG ACT TTC CAG CAC GTG AAG ATG ACC CCC AGT
 S   L   S   K   S   V   T   L   T   F   Q   H   V   K   M   T   P   S 927            936            945            954            963            972
ACC AAA TCC AAG GTC TTC TGT GTC TAC TGG AAG AGC ACA GGG CAG AGC CAG TGG
 T   K   S   K   V   F   C   V   Y   W   K   S   T   G   Q   S   Q   W 981            990            999            1008           1017           1026
TCC AGG GAT GGC TGC CAG TTC CTG ATA CAC GTG AAC AAG AGT CAC ACC ATG TGT AAT
 S   R   D   G   C   Q   F   L   I   H   V   N   K   S   H   T   M   C   N 1035           1044           1053           1062           1071           1080
TGC AGT CAC CTG TCC AGC TGT GTC TTC GCT GCC CTG ATG GCC AGC CAG GAG GAG
 C   S   H   L   S   S   C   V   F   A   A   L   M   A   S   Q   E   E 1089           1098           1107           1116           1125           1134
GAT CCC GTG CTG ACT GTC ATC ACC TAC GTG GGG CTG AGC GTC TCT CTG CTG TGC
 D   P   V   L   T   V   I   T   Y   V   G   L   S   V   S   L   L   C
```

FIGURE 1C

```
     1143             1152             1161             1170             1179             1188
CTC  CTC  GCG  GCC  CTC  ACT  TTT  CTC  CTG  TGT  AAA  GCC  ATC  CAG  AAC  ACC  AGC
 L    L    A    A    L    T    F    L    L    C    K    A    I    Q    N    T    S 1197             1206             1215             1224             1233             1242
ACC  TCA  CTG  CAT  CTG  CAG  CTC  TCG  CAG  CTC  TGC  CTC  CTG  GCC  CAC  CTC  CTC  TTC
 T    S    L    H    L    Q    L    S    Q    L    C    L    L    A    H    L    L    F 1251             1260             1269             1278             1287             1296
CTC  GTG  GGG  ATT  GAT  CGA  ACT  GAA  CCC  AAG  GTG  CTG  TGC  TCC  ATC  ATC  GCC  GGT
 L    V    G    I    D    R    T    E    P    K    V    L    C    S    I    I    A    G 1305             1314             1323             1332             1341             1350
GCT  TTG  CAC  TAT  CTC  ACT  GCC  TAC  CTG  GCC  TTC  ACC  ATG  CTG  GAG  GGT  GTG
 A    L    H    Y    L    T    A    Y    L    A    F    T    M    L    E    G    V 1359             1368             1377             1386             1395             1404
CAC  CTC  TTC  CTC  ACT  GCA  CGG  AAC  CTG  ACA  GTC  GTC  AAC  TAC  AGC  ATC  AAT
 H    L    F    L    T    A    R    N    L    T    V    V    N    Y    S    I    N 1413             1422             1431             1440             1449             1458
AGA  CTC  ATG  AAG  TGG  ATC  ATG  TTC  CCA  GTC  GGC  TAT  GGC  GTT  CCC  GCT  GTG  ACT
 R    L    M    K    W    I    M    F    P    V    G    Y    G    V    P    A    V    T 1467             1476             1485             1494             1503             1512
GTG  GCC  ATT  TCT  GCA  GCC  TCC  TGG  CCT  CAC  CTT  TAT  GGA  ACT  GCT  GAT  CGA  TGC
 V    A    I    S    A    A    S    W    P    H    L    Y    G    T    A    D    R    C
```

FIGURE 1D

```
    1521              1530              1539              1548              1557              1566
TGG CTC CAC CTG GAC CAG GGA TTC ATG TGG AGT TTC CTT GGC CCA GTC TGT GCC
 W   L   H   L   D   Q   G   F   M   W   S   F   L   G   P   V   C   A 1575              1584              1593              1602              1611              1620
ATT TTC TCT GCG AAT TTA GTA TTG TTT ATC TTG GTC TTT TGG ATT TTG AAA AGA
 I   F   S   A   N   L   V   L   F   I   L   V   F   W   I   L   K   R 1629              1638              1647              1656              1665              1674
AAA CTT TCC CTC AAT AGT GAA GTG TCA ACC ATC CAG AAC ACA AGG ATG CTG
 K   L   S   L   N   S   E   V   S   T   I   Q   N   T   R   M   L 1683              1692              1701              1710              1719              1728
GCT TTT AAA GCA ACA GCT CAG CTC TTC ATC CTG GGC TGC ACA TGG TGT CTG GGC
 A   F   K   A   T   A   Q   L   F   I   L   G   C   T   W   C   L   G 1737              1746              1755              1764              1773              1782
TTG CTA CAG GTG GGT CCA GCC GCC CAG GTC ATG GCC TAC CTC TTC ACC ATC ATC
 L   L   Q   V   G   P   A   A   Q   V   M   A   Y   L   F   T   I   I 1791              1800              1809              1818              1827              1836
AAC AGC CTC CAA GGC TTC TTC ATC TTC TTG GTC TAC TGC CTC CTC AGC CAG CAG
 N   S   L   Q   G   F   F   I   F   L   V   Y   C   L   L   S   Q   Q 1845              1854              1863              1872              1881              1890
GTC CAG AAA CAA TAT CAA AAG TGG TTT AGA GAG ATC GTA AAA TCA AAA TCT GAG
 V   Q   K   Q   Y   Q   K   W   F   R   E   I   V   K   S   K   S   E
```

FIGURE 1E

```
      1899      1908      1917      1926      1935      1944
TCT GAG ACA TAC ACA CTT TCC AGC AAG ATG GGT CCT GAC TCA AAA CCC AGT GAG
 S   E   T   Y   T   L   S   S   K   M   G   P   D   S   K   P   S   E 1953      1962      1971      1980      1989      1998
GGG GAT GTT TTT CCA GGA CAA GTG AAG AGA AAA TAT TAA AAC TAG AAT ATT CAA
 G   D   V   F   P   G   Q   V   K   R   K   Y 2007      2016      2025      2034      2043      2052
CTC CAT ATG GAA AAT CAT ATC CAT GGA TCT CTT TGG CAT TAT GAA GAA TGA AGC 2061      2070      2079      2088      2097      2106
TAA GGA AAA GGG AAT TCA TTA AAC ATA TCA TCC TTG GAG AGG AAG TAA TCA ACC 2115      2124      2133      2142      2151      2160
TTT ACT TCC CAA ACT GTT TGT TCT CAA ACT GCT CTC AAC AAA TGT GTG GTA 2169      2178      2187      2196      2205      2214
AAT TGC ATT TCT CTT CAC TAT GGT GTA TTC AGT CAA TGC TTG TCC CTG GAA ACC 2223      2232      2241      2250      2259      2268
CAA AGC ATG ACC ACT GCA AAT ATT TCC TTG ACT TTT TGT AAA TGA AGA GGT CCT 2277      2286      2295      2304      2313      2322
TTT CCT CAA GTT CTT AGT CCC ACT CAT CCT AAA CTT GCT CTT TTA AGA CAG 2331      2340      2349      2358      2367      2376
AGT TTC ACT CTG TCA CCC AGG CTG GAG TGT AGT GGC ATG ATC GTA GCT CAC TGC
```

FIGURE 1F

```
                  2385             2394             2403             2412             2421             2430
AGC CTC AAA CTC CAG AGC TCA ACT GGT TCT CCA GCC TCA GCT TCC CAA AGT GCT 2439             2448             2457             2466             2475             2484
GGG ATT ACA GGC ATG AGC CAC TGC ACC TGG CCA TAA ACT TGC TCT TTA AAC TCA 2493             2502             2511             2520             2529             2538
CTC ATT CCC TCA AAC CAT CAG CTT CCT ACT GGC TTT ACT TCC TTG CTA GAT ACA 2547             2556             2565             2574             2583             2592
GGC TAA TTT TTT TTT TTT TTT TTT TTT GAG ATG GAG TTT CGC TCT TGT 2601             2610             2619             2628             2637             2646
TGC CCA GGC TGG AGT GCA ACG GCG TGA GTG CAA CCT CTG CCT CCC GGG TTC AAG 2655             2664             2673             2682             2691             2700
CGA TTC TTC TGC CTC AGC CTC CCA AGT AGC TGG CGT TAC AGG TAT GGA CCA CCA 2709             2718             2727             2736             2745             2754
TGT CCG GCT AAT TTT GTA TTT TTA GTA GAG ACA GGG TTT CTC CAT GTT GGT CAG 2763             2772             2781             2790             2799             2808
GCT CTC GAA CTC CCA GCC TCA GGT GAT CCA CCT GAC TTG GCC TCC CAA GAG 2817             2826             2835             2844             2853             2862
TGT TGG GAT TAC AGG CAT GAG CCA CCG TGC CCA GCC CAG GCT AAC TTA TTT TCT
```

FIGURE 1G

```
     2871        2880        2889        2898        2907        2916
TCT GAG ACT GAG TCT CAC TAC TGT CAC CCA GGC TGG AGT GCA GTG GTG AGA TCT 2925        2934        2943        2952        2961        2970
AGG CTC ACT GCA ACC TCT ACC TCC TGG GTT CAA GCA ATT CTC CTG CCT TAG CCT 2979        2988        2997        3006        3015        3024
CCC GAT AGC TGG GAC TAC AAG CAC ATG CCG CCA TGC CCA GCT AAT TTT GTA TTT 3033        3042        3051        3060        3069        3078
TTA GTG GAG ACA AGG TTT CAC CAT GTT GGC CAG GCT GAT CTC AAA CTC CTG ACC 3087        3096        3105        3114        3123        3132
TCA AGC AGC GAT CCA CCT GCC GGG GCC TCC CAA AGT GCT GGG ATT ACA GAC ACA 3141        3150        3159        3168        3177        3186
AGC CAT CGC GCC TGA TGA GAG ATT TTA AGT GTT CTC ACC ACA AAA AAA AAG AAA 3195        3204        3213        3222        3231        3240
AAA AAG TTA TAT GAG GTA ATC GTA TAT TAA TTA GCT TGA CTT AGT CAT TCC ACG 3249        3258        3267        3276        3285        3294
ATG TAG ATA TAT TTC AAA ACA TCC TGT TGT ACA TGA TAA ATA TAT ATA TTT TNG 3303        3312        3321        3330        3339        3348
TCT ATA TAA AAC AAA TAA ATA AAT AAA TGT TTA AAG TGT AAA AAA AAA AAA AAA

```
295 MTPSTKKVFCVYWKSTGQGSQ-WSRDGCFL  429905
541 PKQKFERPICVSWSTDVKGGR-WTSFGCVI  GI 784994
  1 ----KVLCVFWEHGQNGCGHWATTGCST  GI 2935597

324 IHVNKSHTMCNCSHLSSFAVLMALTSQEED  429905
570 LEASETYTICSCNQMANLAVIMASGELTMD  GI 784994
 25 IGTRDTSTICRCTHLSSFAVLMAHYDVQED  GI 2935597

354 PVLTVITYVGLSVSLLCLLLAALTFLLCKA  429905
600 FSLYIISHVGIIISLVCLVLAIATFLLCRS  GI 784994
 55 PVLTVITYMGLSVSLLCLLLAALTFLLCKA  GI 2935597

384 IQNTSTSLHLQLSLCLFLAHLLFLVGIDRT  429905
630 IRNHNTYLHLHLCVCLLLAKTLFLAGIHKT  GI 784994
 85 IQNTSTSLHLQLSLCLFLAHLLFLVAIDQT  GI 2935597

414 EPKVLCSIIAGALHYLYLAAFTWMLLEGVH  429905
660 DNKTGCAIIAGFLHYLFLACFFWMLVEAVI  GI 784994
115 GHKVLCSIIAGTLHYLYLATFTWMLLEALY  GI 2935597

444 LFLTARNLTVVNYSSINRLMKWIMFPVGYG  429905
690 LFLMVRNLKVVNYFSSRNIKMLHICAFGYG  GI 784994
145 LFLTARNLTVVNYSSINRFMKKLMFPVGYG  GI 2935597
```

```
474  V P A V T V A I S A A S W P H L Y G T A D R C W L H L D Q G    429905
720  L P M L V V V I S A S V Q P Q G Y G M H N R C W L N T E T G    GI 784994
175  V P A V T V A I S A A S R P H L Y G T P S R C W L Q P E K G    GI 2935597

504  F M W S F L G P V C A I F S A N L V F I L V F W I L K R K     429905
750  F I W S F L G P V C T V I V I N S L L T W T L W I L R Q R     GI 784994
205  F I W G F L G P V C A I F S V N L V F L V T L W I L K N R     GI 2935597

534  L S S L N S E V S T I Q N T R M L A F K A T A Q L F I L G C   429905
780  L S S V N A E V S T L K D T R L L T F K A F A Q L F I L G C   GI 784994
235  L S S L N S E V S T L R N T R M L A F K A T A Q L F I L G C   GI 2935597

564  T W C L G L L Q V G P A A Q V M A Y L F T I I N S L Q G F F   429905
810  S W V L G I F Q I G P V A G V M A Y L F T I I N S L Q G A F   GI 784994
265  T W C L G I L Q V G P A A R V M A Y L F T I I N S L Q G V F   GI 2935597

594  I F L V Y C L L S Q Q V Q K Q Y Q K W F R E I V K S K S E S   429905
840  I F L I H C L L N G Q V R E E Y K R W I T G K T K P S S Q S   GI 784994
295  I F L V Y C L L S Q Q V R E Q Y G K W S K G I R K L K T E S   GI 2935597

624  E T Y - T L S S K M G P D S K P S E G D V F P G Q V K R K Y   429905
870  Q T S R I L L S S M P S A S K T G                             GI 784994
325  E M H T L S S A K A D T S K P S T V N                         GI 2935597
```

FIGURE 2E

HUMAN EMR1-LIKE G PROTEIN COUPLED RECEPTOR

FIELD OF THE INVENTION

This invention relates to nucleic acid and amino acid sequences of a human Emr1-like G protein coupled receptor and to the use of these sequences in the diagnosis, treatment, and prevention of respiratory, inflammatory, and immunological disorders.

BACKGROUND OF THE INVENTION

Inflammation is a molecular, cellular, and tissue program during which foreign substances and pathogens are destroyed, and injured tissue is repaired through a variety of biochemical, biophysical, and cellular mechanisms. The principal cellular mediators of inflammation are leukocytes. Two main classes of leukocytes that sustain the inflammatory processes are granulocytes and monocytes/macrophages. Macrophages form an important part of the mammalian host defense system in normal and pathological processes.

Macrophages are derived from a pool of monocytes that have migrated into peripheral tissues such as those of the liver, spleen, lung, lymph nodes, peritoneum, skin, brain, and bone, where they differentiate into macrophages. The major characteristic of macrophages is their ability to recognize, internalize, and destroy a variety of foreign (non-self) and endogenous substances and pathogens including bacteria, parasites, and viruses. The exact recognition mechanism for non-self pathogens is unknown, but it has been proposed that receptors with broad binding specificity are used to discriminate between self and non-self antigens. Macrophages are also thought to play an important role in the immune response by presenting foreign antigens to lymphocytes.

Signal transduction is the general process by which cells respond to extracellular signals. Extracellular signals are mediated through a biochemical cascade that begin with the binding, of a signal molecule, e.g., a hormone, neurotransmitter, or growth factor, to a cell membrane receptor and end with the activation of an intracellular target molecule. This process of signal transduction regulates all types of cell functions including cell proliferation, differentiation, and gene transcription.

GTP binding protein (G protein) signaling is one of the important biochemical pathways of signal transduction. G protein coupled receptors (GPCR) are a superfamily of integral membrane proteins which transduce extracellular signals. GPCRs include receptors for biogenic amines; for lipid mediators of inflammation, peptide hormones, and sensory signal mediators. The GPCR becomes activated when the receptor binds its extracellular ligand. Conformational chances in the GPCR which result from the ligand-receptor interaction affect the binding affinity of a G protein to the GPCR intracellular domains. This enables GTP to bind with enhanced affinity to the G protein. Activation of the G protein by GTP leads to the interaction of the G protein $\alpha$ subunit with adenylate cyclase or other second messenger molecule generator. This interaction regulates the activity of adenylate cyclase and hence production of a second second messenger molecule, cAMP. cAMP regulates phosphorylation and activation of other intracellular proteins. Alternatively, cellular levels of other second messenger molecules, such as, for example, cGMP or eicosinoids, may be upregulated or downregulated by the activity of GPCRs. The G protein $\alpha$ subunit is deactivated by hydrolysis of the GTP by GTPase and the $\beta\gamma$ and $\alpha$ subunits reassociate. The heteromeric G protein then dissociates from the adenylate cyclase or other second messenger molecule generator. Activity of GPCR may also be regulated by phosphorylation of the intra- and extracellular domains or loops.

The structure of these highly-conserved receptors consists of seven hydrophobic transmembrane (serpentine) regions, cysteine disulfide bridges between the second and third extracellular loops, an extracellular N-terminus, and a cytoplasmic C-terminus. Three extracellular loops alternate with three intracellular loops to link the seven transmembrane regions. The most conserved parts of these proteins are the transmembrane regions and the first two cytoplasmic loops. A conserved, acidic-Arg-aromatic residue triplet present in the second cytoplasmic loop may interact with the G-proteins. The consensus pattern of the G-protein coupled receptors signature (PS00237; SWISSPROT) is characteristic of most proteins belonging to this superfamily (Watson, S. and S. Arkinstall (1994) *The G-protein Linked Receptor Facts Book*, Academic Press, San Diego, Calif., pp 2–6).

Examples of GPCRs implicated in inflammation and the immune response include the EGF module-containing, mucin-like hormone receptor (Emr1) and CD97$\beta$ receptor proteins. These seven transmembrane hormone receptors exist as heterodimers in vivo and contain between three and seven potential calcium-binding EGF-like motifs (Baud, V. et al. (1995) Genomics 26:334–344; Gray, J. X. et al. (1996) J. Immunol. 157:5438–5447). In addition, an orphan Emr1-like GPCR (g2935597, NCBI GenBank) has recently been mapped to human chromosome 19. These GPCRs are members of the recently characterized EGF-TM7 receptors family.

The discovery of a new human Emr1-like G protein coupled receptor and the polynucleotides encoding it satisfies a need in the art by providing new compositions which are useful in the diagnosis, treatment, and prevention of respiratory, inflammatory, and immunological disorders.

SUMMARY OF THE INVENTION

The invention is based on the discovery of a new human Emr1-like G protein coupled receptor (EGPCR), the polynucleotides encoding EGPCR, and the use of these compositions for the diagnosis, treatment, or prevention of respiratory, inflammatory, and immunological disorders.

The invention features a substantially purified polypeptide comprising the amino acid sequence of SEQ ID NO:1 or a fragment of SEQ ID NO:1.

The invention further provides a substantially purified variant having at least 90% amino acid sequence identity to the amino acid sequence of SEQ ID NO:1 or a fragment of SEQ ID NO:1. The invention also provides an isolated and purified polynucleotide encoding the polypeptide comprising the sequence of SEQ ID NO:1 or a fragment of SEQ ID NO:1. The invention also includes an isolated and purified polynucleotide variant having at least 70% polynucleotide sequence identity to the polynucleotide encoding the polypeptide comprising the amino acid sequence of SEQ ID NO:1 or a fragment of SEQ ID NO:1.

The invention further provides an isolated and purified polynucleotide which hybridizes under stringent conditions to the polynucleotide encoding the polypeptide comprising the amino acid sequence of SEQ ID NO:1 or a fragment of SEQ ID NO:1, as well as an isolated and purified polynucleotide which is complementary to the polynucleotide encoding the polypeptide comprising the amino acid sequence of SEQ ID NO:1 or a fragment of SEQ ID NO:1.

The invention also provides an isolated and purified polynucleotide comprising the polynucleotide sequence of SEQ ID NO:2 or a fragment of SEQ ID NO:2, and an isolated and purified polynucleotide variant having at least 70% polynucleotide sequence identity to the polynucleotide comprising the polynucleotide sequence of SEQ ID NO:2 or a fragment of SEQ ID NO:2. The invention also provides an isolated and purified polynucleotide having a sequence complementary to the polynucleotide comprising the polynucleotide sequence of SEQ ID NO:2 or a fragment of SEQ ID NO:2.

The invention further provides an expression vector comprising at least a fragment of the polynucleotide encoding the polypeptide comprising the sequence of SEQ ID NO:1 or a fragment of SEQ ID NO:1. In another aspect, the expression vector is contained within a host cell.

The invention also provides a method for producing a polypeptide comprising the amino acid sequence of SEQ ID NO:1 or a fragment of SEQ ID NO:1, the method comprising the steps of: (a) culturing the host cell comprising an expression vector containing at least a fragment of a polynucleotide encoding the polypeptide comprising the amino acid sequence of SEQ ID NO:1 or a fragment of SEQ ID NO:1 under conditions suitable for the expression of the polypeptide; and (b) recovering the polypeptide from the host cell culture.

The invention also provides a pharmaceutical composition comprising a substantially purified polypeptide having the sequence of SEQ ID NO:1 or a fragment of SEQ ID NO:1 in conjunction with a suitable pharmaceutical carrier.

The invention further includes a purified antibody which binds to a polypeptide comprising the sequence of SEQ ID NO:1 or a fragment of SEQ ID NO:1, as well as a purified agonist and a purified antagonist of the polypeptide.

The invention also provides a method for treating or preventing a disorder associated with decreased expression or activity of EGPCR, the method comprising administering to a subject in need of such treatment an effective amount of a pharmaceutical composition comprising substantially purified polypeptide having the amino acid sequence of SEQ ID NO:1 or a fragment of SEQ ID NO:1.

The invention also provides a method for treating or preventing a disorder associated with increased expression or activity of EGPCR, the method comprising administering to a subject in need of such treatment an effective amount of an antagonist of the polypeptide having the amino acid sequence of SEQ ID NO:1 or a fragment of SEQ ID NO:1.

The invention also provides a method for detecting a polynucleotide encoding a polypeptide comprising the amino acid sequence of SEQ ID NO:1 or a fragment of SEQ ID NO:1 in a biological sample containing nucleic acids, the method comprising the steps of: (a) hybridizing the complement of the polynucleotide encoding the polypeptide comprising the amino acid sequence of SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding the polypeptide comprising the amino acid sequence of SEQ ID NO:1 or a fragment of SEQ ID NO:1 in the biological sample. In one aspect, this method further comprises amplifying the polynucleotide prior to hybridization.

BRIEF DESCRIPTION OF THE FIGURES AND TABLES

FIGS. 1A, 1B, 1C, 1D, 1E, 1F, 1G, and 1H show the amino acid sequence (SEQ ID NO:1) and nucleic acid sequence (SEQ ID NO:2) of EGPCR. The alignment was produced using MACDNASIS PRO software (Hitachi Software Engineering Co. Ltd., San Bruno, Calif.).

FIGS. 2A, 2B, 2C, 2D, and 2E show the amino acid sequence alignments among EGPCR (429905; SEQ ID NO:1), human Emr1 (GI 784994; SEQ ID NO:3), and human orphan Emr1-like GPCR (GI 2935597; SEQ ID NO:4), produced using the multisequence alignment program of LASERGENE software (DNASTAR Inc, Madison, Wis.).

FIG. 3 shows the northern blot autoradiograph of EGPCR expression in different human tissue samples. The tissue source of the mRNA is listed above each lane. The position of standard molecular weight polynucleotide markers are to the left of the autoradiograph. The position of the two EGPCR mRNA species are shown by two arrows to the right of the autoradiograph.

Figure 4:
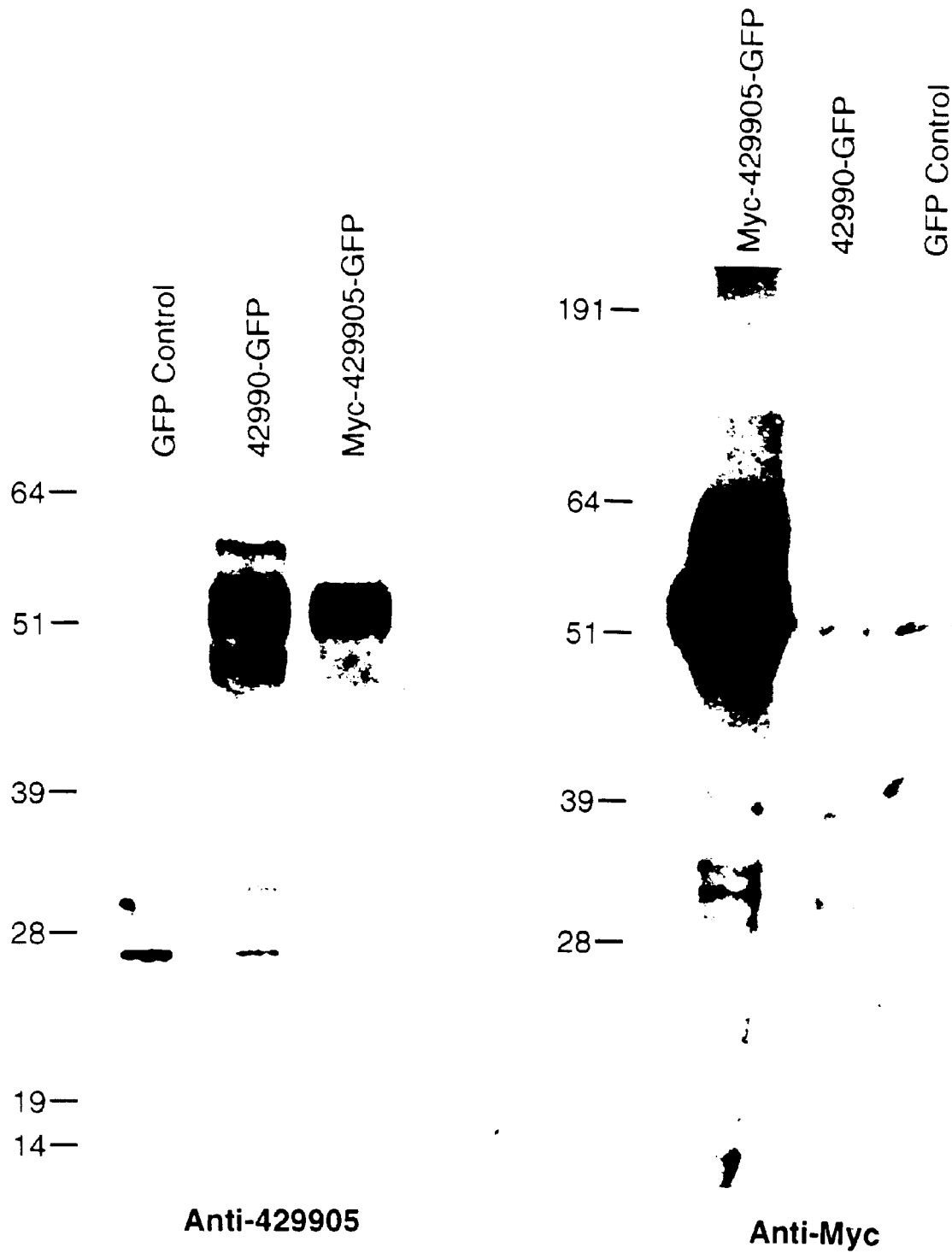

FIG. 4 shows western blot immunoautoradiographs of EGPCR in HEK 293 cell lysates following transfection of HEK 293 cells with a vector containing an EGPCR fragment-green fluorescent protein construct (EF-GFP) or Myc-EF-GFP. The blots were immunostained using either anti-EGPCR antibody (Anti-429905) or anti-Myc antibody (Anti-Myc). The description above each lane describes which plasmid construct was used to transfect the cells. The position of standard molecular weight protein markers are listed to the left of the autoradiogaphs.

Figure 5:
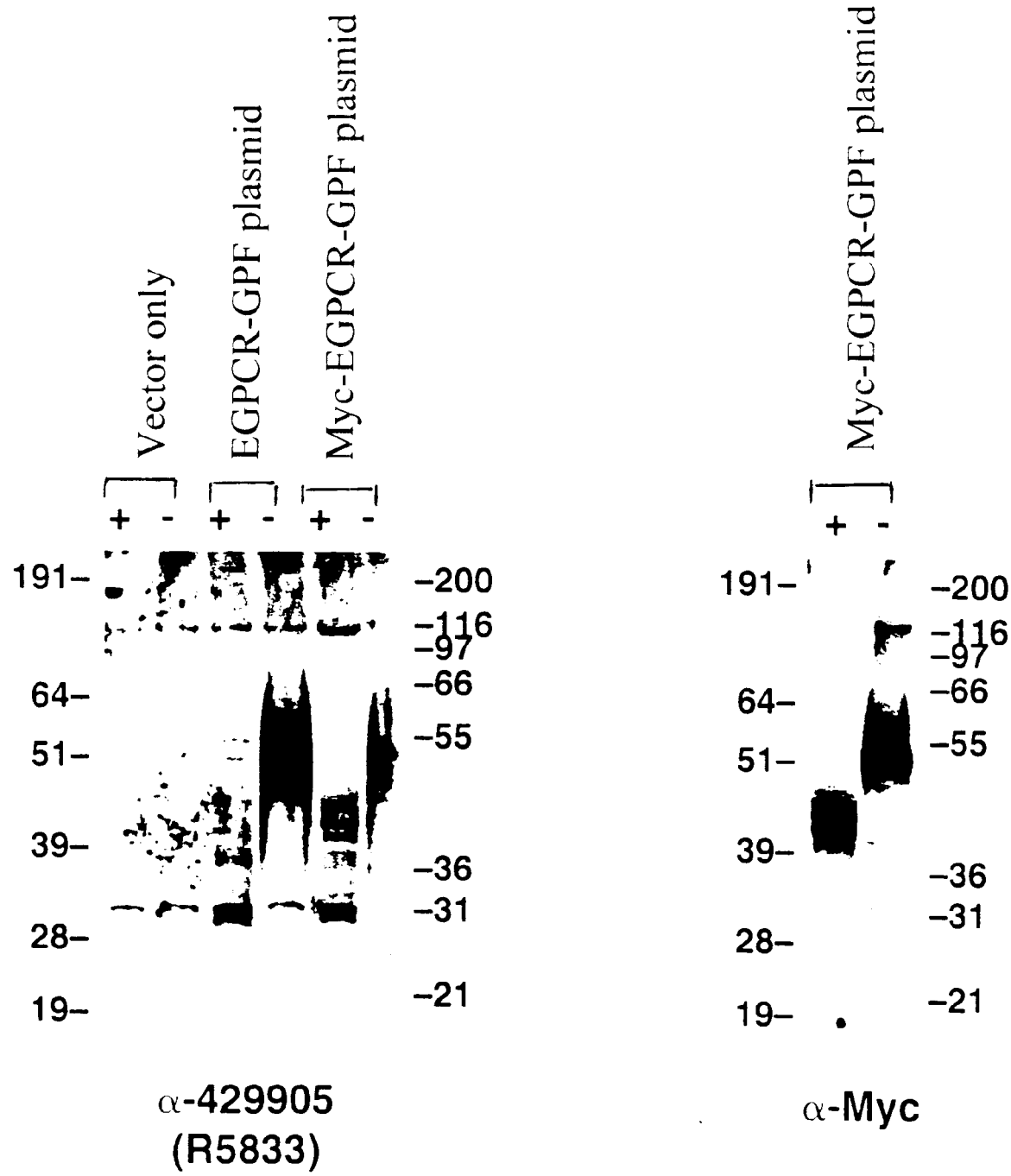

FIG. 5 shows western blot immunoautoradiographs of EF-GFP-transfected HEK 293 cell lysate treated with or without N-glycosylase. The blots were immunostained using either anti-EGPCR antibody (α-429905; R5833) or anti-Myc antibody (α-Myc). The description above each lane describes which plasmid construct was used to transfect the cells. Samples were untreated (−) or treated (+) with N-glycosylase. The position of standard molecular weight protein markers are the left of the autoradiograph.

Table 1 shows the electronic northern blot analysis of EGPCR using the LIFESEQ database (IncytePharmaceuticals, Palo Alto, Calif.). The first column of Table 1 lists the polypeptide sequence identifier (SEQ ID NO). The second column lists the tissue expression of EGPCR and fraction of total tissue which express SEQ ID NO:1. The third column lists the disease class and fraction of total disease tissues that express SEQ ID NO:1.

Table 2 summarizes the programs/algorithms, descriptions of the programs, references, and threshold parameters (where applicable) used to analyze EGPCR.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"EGPCR" refers to the amino acid sequences, or variant thereof, of substantially purified EGPCR obtained from any species, particularly a mammalian species, including bovine, ovine, porcine, murine, equine, and preferably the human species, from any source, whether natural, synthetic, semi-synthetic, or recombinant.

"Agonist" refers to a molecule which, when bound to EGPCR, increases or prolongs the duration of the effect of EGPCR. Agonists may include proteins, nucleic acids, carbohydrates, or any other molecules which bind to and modulate the effect of EGPCR.

An "allelic variant" is an alternative form of the gene encoding EGPCR. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding EGPCR include those sequences with deletions, insertions, or substitutions of different nucleotides, resulting in a polynucleotide the same as EGPCR or a polypeptide with at least one functional characteristic of EGPCR. Included within this definition are polymorphisms which may or may not be readily detectable using a particular oligonucleotide probe of EGPCR, and improper or unexpected hybridization to allelic variants, with a locus other than the normal chromosomal locus for the polynucleotide sequence encoding EGPCR. The encoded protein may also be "altered," and may contain deletions, insertions, or substitutions of amino acid residues which produce a silent change and result in a functionally equivalent EGPCR. Deliberate amino acid substitutions may be made on the basis of similarity in polarity, charge, solubility, hydrophobicity, hydrophilicity, and/or the amphipathic nature of the residues, as long as the biological or immunological activity of EGPCR is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

"Amino acid" or "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of EGPCR which are preferably at least 5 to about 15 amino acids in length, most preferably at least 14 amino acids, and which retain some biological activity or immunological activity of EGPCR.

"Amplification" refers to the production of additional copies of a nucleic acid sequence. Amplification is generally carried out using polymerase chain reaction (PCR) technologies well known in the art.

"Antagonist" refers to a molecule which, when bound to EGPCR, decreases the amount or the duration of the effect of the biological or immunological activity of EGPCR. Antagonists may include proteins, nucleic acids, carbohydrates, antibodies, or any other molecules which decrease the effect of EGPCR.

"Antibody" refers to intact molecules as well as to fragments thereof, such as Fab, F(ab'), and Fv fragments, which are capable of binding the epitopic determinant. Antibodies that bind EGPCR polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

"Antigenic determinant" refers to that fragment of a molecule, an epitope, that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen, the immunogen used to elicit the immune response, for binding to an antibody.

"Antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

"Biologically active" refers to a molecule having structural, regulatory, or biochemical functions of a naturally occurring, molecule. Likewise, "immunologically active" refers to the capability of the natural, recombinant, or synthetic EGPCR, or of any oligopeptide thereof, to induce a specific immune response in appropriate animals or cells and to bind with specific antibodies.

"Complementary" or "complementarity" refer to the natural binding of polynucleotides by base pairing. For example, the sequence "5' A-G-T 3'" binds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between two nucleic acid strands has significant effects on the efficiency and strength of the hybridization between them. This is of particular importance in amplification reactions, which depend upon binding between nucleic acids strands, and in the design and use of peptide nucleic acid (PNA) molecules.

A "composition" refers broadly to any composition containing the given polynucleotide or amino acid sequence.

The composition may comprise a dry formulation or an aqueous solution. Compositions comprising polynucleotide sequences encoding EGPCR or fragments of EGPCR may be employed as hybridization probes. The probes may be stored in freeze-dried form and may be associated with a stabilizing agent such as a carbohydrate. In hybridizations, the probe may be deployed in an aqueous solution containing salts, detergents, and other components, e.g., Denhardt's solution, dry milk, salmon sperm DNA, etc.

"Consensus sequence" refers to a nucleic acid sequence which has been resequenced to resolve uncalled bases, extended using XL-PCR (Perkin Elmer, Norwalk, Conn.) in the 5' and/or the 3' direction, and resequenced, or assembled from the overlapping sequences of more than one Incyte Clone using a computer program for fragment assembly, such as the GELVIEW fragment assembly system (GCG, Madison, Wis.). Some sequences have been both extended and assembled to produce the consensus sequence.

The term "correlates with expression of a polynucleotide" indicates that the detection of the presence of nucleic acids, the same or related to a nucleic acid sequence encoding EGPCR, by Northern analysis is indicative of the presence of nucleic acids encoding EGPCR in a sample, and thereby correlates with expression of the transcript from the polynucleotide encoding EGPCR.

"Deletion" refers to a change in the amino acid or nucleotide sequence that results in the absence of one or more amino acid residues or nucleotides.

"Derivative" refers to the chemical modification of a polypeptide or polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

"Similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific, selective interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically using the MEGA-LIGN program (DNASTAR, Inc., Madison, Wis.). Alignments can be created between two or more sequences using different methods, e.g., the clustal method (Higgins, D. G. and P. M. Sharp (1988) Gene 73:237–244). The clustal algorithm groups sequences into clusters by examining the distances between all pairs. The clusters are aligned pairwise and then in groups. The percentage similarity between two amino acid sequences is calculated by dividing the length of the first sequence, minus the number of gap residues in that sequence, minus the number of gap residues in the second sequence, into the sum of the residue matches between the sequences, times one hundred. Gaps of low or of no similarity between the two amino acid sequences are not included in determining percentage similarity. Percent identity between nucleic acid sequences can also be counted or calculated by other methods known in the art, e.g., the Jotun Hein method (Hein, J. (1990) Methods Enzymol. 183:626–645). Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

"Humanized antibody" refers to antibody molecules in which the amino acid sequence in the non-antigen binding regions has been altered so that the antibody more closely resembles a human antibody and still retains its original binding ability.

"Hybridization" refers to any process by which a strand of nucleic acid binds with a complementary strand by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on an appropriate substrate.

"Insertion" or "addition" refer to changes in an amino acid or nucleotide sequence resulting in the incorporation of one or more amino acid residues or nucleotides, respectively, to the sequence found in the naturally occurring molecule.

"Immune response" refers to conditions associated with inflammation, trauma, immune disorders, or infectious or genetic disease, etc. These conditions can be characterized by expression of various factors, e.g., cytokines, chemokines, and other signaling molecules, which affect cellular and systemic defense systems.

"Microarray" refers to an arrangement of distinct polynucleotides on a substrate. Similarly, "element" or "array element" refer to hybridizable polynucleotides arranged on a substrate.

"Modulate" refers to a change in the activity of EGPCR. For example, modulation may cause an increase or a decrease in activity, binding characteristics, or any other biological, functional, or immunological properties of EGPCR.

"Nucleic acid" or "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, antigenicity, or a structural characteristic of the full-length polypeptide.

"Operably associated" or "operably linked" refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

"Oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. An oligonucleotide is substantially equivalent to the terms "amplimer," "primer," "oligomer," and "probe," as commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell (Nielsen, P. E. et al. (1993) Anticancer Drug Des. 8:53–63).

"Sample" is used herein in its broadest sense and may comprise a bodily fluid; an extract from a cell, chromosome, organelle, or membrane isolated from a cell; a cell; genomic DNA, RNA, or cDNA, in solution or bound to a solid support; a tissue; a tissue print; etc.

"Specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

"Stringent conditions" refers to conditions which permit hybridization between polynucleotides and the claimed polynucleotides. Stringent conditions can be defined by salt concentration and temperature. In some membrane-based hybridizations, these conditions may be modified; e.g. temperature may be lowered if an organic solvent such as formamide is added to the solution). In general, stringency can be increased by reducing the concentration of salt or raising the hybridization temperature.

"Substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which the polynucleotide probes are bound.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of EGPCR polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to EGPCR. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional sequence or functional domains or an absence of sequence or domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

THE INVENTION

The invention is based on the discovery of a new human Emr1-like G protein coupled receptor (EGPCR), the polynucleotides encoding EGPCR, and the use of these compositions for the diagnosis, treatment, or prevention of respiratory, inflammatory, and immunological disorders.

Nucleic acids encoding the 3350 bp full length EGPCR of the present invention were first identified in Incyte Clone 429905 from the eosinophil cDNA library (EOSINOT03).

In one embodiment, the invention encompasses a polypeptide comprising the amino acid sequence of SEQ ID NO:1, as shown in FIGS. 1A, 1B, 1C, 1D, 1E, 1F, 1G, and 1H. EGPCR is 652 amino acids in length and has a predicted molecular mass of approximately 72.6 kDa. EGPCR has twelve potential N-glycosylation sites at residues N34, N39, N145, N189, N202, N250, N279, N327, N334, N386, N450, and N455; one potential cAMP- and cGMP-dependant protein kinase phosphorylation site at residue S535; nine potential casein kinase II phosphorylation sites at residues T64, S104, T116, T252, T348, S349, S619, S621, and S639; one potential glycosaminoglycan attachment site at residue S51; six potential protein kinase C phosphorylation sites at residues T21, S122, S298, T299, T447, and S629; one potential tyrosine kinase phosphorylation site at residue Y626; one potential aspartic acid and asparagine hydroxylation site at residue N87; two Type II EGF-like signatures from residues C28 to C66 and C72 to C117; one Type I EGF-like signature from residues C304 to C370; and the G-protein coupled receptor motifs from residues C381 to I410, C419 to A448, M505 to S535, and S588 to F613. As shown in FIGS. 2A, 2B, 2C, 2D, and 2E, EGPCR has chemical and structural similarity with human Emr1 (GI 784994; SEQ ID NO:3), and human orphan Emr1-like GPCR (GI 2935597; SEQ ID NO:4). In particular, EGPCR and human orphan Emr1-like GPCR share 57% identity, two potential N-glycosylation sites, the potential cAMP- and cGMP-dependant protein kinase phosphorylation site, two potential casein kinase II phosphorylation sites, three potential protein kinase C phosphorylation sites, the aspartic acid and asparagine hydroxylation site, the type I EGF-like signature, and the G-protein coupled receptor motifs. A fragment of SEQ ID NO:2 from about nucleotide 1399 to about nucleotide 1428 is useful, for example, for designing oligonucleotides or as a hybridization probe.

A hydropathy plot analysis of EGPCR revealed an N-terminal signal peptide followed by an extracellular domain of 350 residues, seven hydrophobic potential transmembrane regions, and a C-terminal 320 amino acid residues. The structural features of a GPCR and sequence homology placed EGPCR in the recently defined novel EGF-TM7 receptor subfamily. This subfamily is related to the hormone receptor gene family and includes receptors for glucagon, calcitonin, corticotropin releasing hormone, secretin, VIP, and diuretic hormone. The expression pattern of EGPCR was examined by electronic Northern blot analysis of Incyte cDNA libraries isolated from various tissues and cell types. As shown in Table 1, EGPCR was present in eosinophils, monocytes, and neutrophils. In addition, the expression pattern of EGPCR was examined by Northern blot analysis of RNA isolated from various tissues and cell types. As shown in FIG. 3, EGPCR mRNA was expressed at low level in spleen, peripheral blood leukocytes, and bone marrow. This pattern was consistent with expression in cells or tissues involved in the immune response. Two mRNA species of 3.5 kb and 1.8 kb were observed in tissues expressing EGPCR. In peripheral blood leukocytes, the 1.8 kb species seems to be expressed at a slightly higher levels than in other tissues. It is conceivable that these two species are the results of alternative splicing and the 1.8 kb mRNA species may encode a splice variant of the gene.

An EGPCR fragment-green fluorescent protein (GFP) conjugate was expressed in HEK 293 cells following transfection with EGPCR fragment-GFP-containing vector. As shown in FIG. 4, cell lysates from transfected HEK 293 cells contained a 51–53 kDa band of protein which bound to anti-EGPCR antibody. As shown in FIG. 5, cell lysates from transfected HEK 293 cells that had been treated with N-glycosidase contained an anti-EGPCR-binding protein of approximately 31 kDa. The difference in size between treated and native EGPCR was attributed to postranslational glycosylation.

The invention also encompasses EGPCR variants. A preferred EGPCR variant is one which has at least about 80%, more preferably at least about 90%, and most preferably at least about 95% amino acid sequence identity to the EGPCR amino acid sequence, and which contains at least one functional or structural characteristic of EGPCR.

The invention also encompasses polynucleotides which encode EGPCR. In a particular embodiment, the invention encompasses a polynucleotide sequence comprising the sequence of SEQ ID NO:2, which encodes an EGPCR.

The invention also encompasses a variant of a polynucleotide sequence encoding EGPCR. In particular, such a variant polynucleotide sequence will have at least about 70%, more preferably at least about 80%, and most preferably at least about 95% polynucleotide sequence identity to the polynucleotide sequence encoding EGPCR. A particular aspect of the invention encompasses a variant of SEQ ID NO:2 which has at least about 70%, more preferably at least about 80%, and most preferably at least about 95% polynucleotide sequence identity to SEQ ID NO:2. Any one of the polynucleotide variants described above can encode an amino acid sequence which contains at least one functional or structural characteristic of EGPCR.

It will be appreciated by those skilled in the art that as a result of the degeneracy of the genetic code, a multitude of polynucleotide sequences encoding EGPCR, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring EGPCR, and all such variations are to be considered as being specifically disclosed.

Although nucleotide sequences which encode EGPCR and its variants are preferably capable of hybridizing to the nucleotide sequence of the naturally occurring EGPCR under appropriately selected conditions of stringency, it may be advantageous to produce nucleotide sequences encoding EGPCR possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding EGPCR and its derivatives without altering the encoded amino acid sequences include the production of RNA transcripts having more desirable properties, such as a greater half-life, than transcripts produced from the naturally occurring sequence.

The invention also encompasses production of DNA sequences which encode EGPCR and EGPCR derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding EGPCR or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency. Stringency as it is commonly used in the art is defined in Wahl, G. M. and S. L. Berger (1987; Methods Enzymol. 152:399–407) and Kimmel, A. R. (1987; Methods Enzymol. 152:507–511). For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing and analysis are well known in the art. The methods may employ such enzymes as the Klenow fragment of DNA polymerase I, SEQUENASE enzyme (Amersham Pharmacia Biotech Ltd., Piscataway, N.J.), Taq polymerase (Perkin Elmer), thermostable T7 polymerase (Amersham Pharmacia Biotech Ltd.), or combinations of polymerases and proofreading exonucleases, such as those found in the ELONGASE amplification system (Life Technologies, Gaithersburg, Md.). Preferably, sequence preparation is automated with machines, e.g., the ABI CATALYSTI 800 (Perkin Elmer) or MICROLAB 2200 (Hamilton Co., Reno, Nev.) in combination with thermal cyclers. Sequencing can also be automated, such as by ABI 373 or 377 sequencing systems (Perkin Elmer) or the MEGABACE 1000 capillary electrophoresis system (Molecular Dynamics, Inc., Sunnyvale, Calif.). Sequences can be analyzed using computer programs and algorithms well known in the art (Ausubel, F. M. et al. (1997; *Short Protocols in Molecular Biology*, John Wiley & Sons, New York, N.Y., unit 7.7; and Meyers, R. A. (1995) *Molecular Biology and Biotechnology*, Wiley VCH, Inc, New York, N.Y.).

The nucleic acid sequences encoding EGPCR may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector (Sarkar, G. (1993) PCR Methods Applic. 2:318–322). Another method, inverse PCR, uses primers that extend in divergent directions to amplify unknown sequence from a circularized template. The template is derived from restriction fragments comprising a known genomic locus and surrounding sequences (Triglia, T. et al. (1988) Nucleic Acids Res. 16:8186). A third method, capture PCR, involves PCR amplification of DNA fragments adjacent to known sequences in human and yeast artificial chromosome DNA (Lagerstrom, M. et al. (1991) PCR Methods Applic. 1:111–119). In this method, multiple restriction enzyme digestions and ligations may be used to insert an engineered double-stranded sequence into a region of unknown sequence before performing PCR. Other methods (e.g., Parker, J. D. et al. (1991) Nucleic Acids Res. 19:3055–306) which may be used to retrieve unknown sequences are known in the art. Additionally, one may use PCR, nested primers, and PromoterFinder libraries (Clontech, Palo Alto, Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software such as GENOTYPER and SEQUENCE NAVIGATOR (Perkin Elmer), and the entire process from loading of samples to computer analysis and electronic data display may be computer controlled. Capillary electrophoresis is especially preferable for sequencing DNA fragments which may be present in limited amounts in a particular sample.

In another embodiment of the invention, polynucleotide sequences or fragments thereof which encode EGPCR may be cloned in recombinant DNA molecules that direct expression of EGPCR, or fragments or functional equivalents thereof, in appropriate host cells. Due to the inherent degeneracy of the genetic code, other DNA sequences which encode substantially the same or a functionally equivalent amino acid sequence may be produced and used to express EGPCR.

The nucleotide sequences of the present invention can be engineered using methods generally known in the art in order to alter EGPCR-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding EGPCR may be synthesized, in whole or in part, using chemical methods well known in the art (Caruthers, M. H. et al. (1980) Nucl. Acids Res. Symp. Ser. 215–223; Horn, T. et al. (1980) Nucl. Acids Res. Symp. Ser. 225–232). Alternatively, EGPCR, or a fragment thereof, may be synthesized using chemical methods. For example, peptide synthesis can be performed using various solid-phase techniques (Roberge, J. Y. et al. (1995) Science 269:202–204). Automated synthesis may be achieved using the ABI 431A peptide synthesizer (Perkin Elmer). Additionally, the amino acid sequence of EGPCR, or any part thereof, may be altered during direct synthesis and/or combined with sequences from other proteins, or any part thereof, to produce a variant polypeptide.

The peptide may be substantially purified by preparative high performance liquid chromatography. (Chiez, R. M. and F. Z. Regnier (1990) Methods Enzymol. 182:392–421). The composition of the synthetic peptides may be confirmed by amino acid analysis or by sequencing (Creighton, T. (1984) *Proteins, Structures and Molecular Properties*, WH Freeman and Co., New York, N.Y.).

In order to express a biologically active EGPCR, the nucleotide sequences encoding EGPCR or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding EGPCR. Such elements may vary in their strength and specificity. Specific initiation signals may also be used to achieve more efficient translation of sequences encoding EGPCR. Such signals include the ATG initiation codon and adjacent sequences, e.g. the Kozak sequence. In cases where sequences encoding EGPCR and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used (Scharf, D. et al. (1994) Results Probl. Cell Differ. 20:125–162).

Methods which are well known to those skilled in the art may be used to construct expression vectors containing sequences encoding EGPCR and appropriate transcriptional and translational control elements. These methods include in vitro recombinant DNA techniques, synthetic techniques, and in vivo genetic recombination (Sambrook, J. et al. (1989) *Molecular Cloning, A laboratory Manual*, Cold Spring Harbor Press, Plainview, N.Y., ch. 4, 8, and 16–17; and Ausubel, supra).

A variety of expression vector/host systems may be utilized to contain and express sequences encoding EGPCR. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with expression vectors containing promoters and other elements from viruses (cauliflower mosaic virus, CMV, or tobacco mosaic virus, TMV) or from bacteria (Ti or pBR322 plasmids); or animal cell systems. The invention is not limited by the host cell employed.

In bacterial systems, a number of cloning and expression vectors may be selected depending upon the use intended for polynucleotide sequences encoding EGPCR. For example, routine cloning, subcloning, and propagation of polynucleotide sequences encoding EGPCR can be achieved using a multifunctional *E. coli* vector such as the PBLUESCRIPT vector (Stratagene, San Diego, Calif.) or pSPORT1 plasmid (Life Technlogies). Ligation of sequences encoding EGPCR into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence (Van Heeke, G. and S. M. Schuster (1989) J. Biol. Chem. 264:5503–5509). When large quantities of EGPCR are needed, e.g. for the production of antibodies, vectors which direct high level expression of EGPCR may be used. For example, vectors containing the strong, inducible T5 or T7 bacteriophage promoter may be used.

Yeast expression systems may be used for production of EGPCR. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation (Ausubel, supra; and Scorer, C. A. et al. (1994) Bio/Technology 12:181–184).

Plant systems may also be used for expression of EGPCR. Transcription of sequences encoding EGPCR may be driven viral promoters, e.g., the 35S and 19S promoters of CaMV used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection (*McGraw Hill Yearbook of Science and Technology* (1992) McGraw Hill, New York, N.Y.; pp. 191–196).

In mammalian cells, a number of viral-based expression systems may be utilized. In cases where an adenovirus is used as an expression vector, sequences encoding EGPCR may be ligated into an adenovirus transcription/translation complex consisting of the late promoter and tripartite leader sequence. Insertion in a non-essential E1 or E3 region of the viral genome may be used to obtain infective virus which expresses EGPCR in host cells (Logan, J. and T. Shenk (1984) Proc. Natl. Acad. Sci. 81:3655–3659). In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes (Harrington, J. J. et al. (1997) Nat Genet. 15:345–355).

For long tern production of recombinant proteins in mammalian systems, stable expression of EGPCR in cell lines is preferred. For example, sequences encoding EGPCR can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively (Wigler, M. et al. (1977) Cell 11:223–232; and Lowy, I. et al. (1980) Cell 22:817–823). Also, antimetabolite, antibiotic, or herbicide resistance can be used as the basis for selection. For example, dhfr confers resistance to methotrexate; neo confers resistance to the aminoglycosides neomycin and G-418; and als and pat confer resistance to chlorsulfuron and phosphinotricin acetyltransferase, respectively (Wigler, M. et al. (1980) Proc. Natl. Acad. Sci. 77:3567–3570; Colbere-Garapin, F. et al (1981) J. Mol. Biol. 150:1–14; and McGraw Hill Yearbook, supra). Additional selectable genes have been described, e.g., trpB and hisD, which alter cellular requirements for metabolites (Hartman, S. C. and R. C. Mulligan (1988) Proc. Natl. Acad. Sci. 85:8047–8051). Visible markers, e.g., anthocyanins, green fluorescent proteins (GFP; CLONITECH), β glucuronidase and its substrate β-D-glucuronoside, or luciferase and its substrate luciferin may be used. These markers can be used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, the presence and expression of the gene may need to be confirmed. For example, if the sequence encoding EGPCR is inserted within a marker gene sequence, transformed cells containing sequences encoding EGPCR can be identified by the absence of marker gene function. Alternatively, a marker gene can be placed in tandem with a sequence encoding EGPCR under the control of a single promoter. Expression of the marker gene in response to induction or selection usually indicates expression of the tandem gene as well.

In general, host cells that contain the nucleic acid sequence encoding EGPCR and that express EGPCR may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of EGPCR using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on EGPCR is preferred, but a competitive binding assay may be employed. These and other assays are well known in the art (Hampton, R. et al. (1990) *Serological Methods, a Laboratory Manual*, APS Press, St Paul, Minn., Section IV; Coligan, J. E. et al. (1997 and periodic supplements) *Current Protocols in Immunology*, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding EGPCR include oligolabeling, nick translation, end-labeling, or PCR amplification using a labeled nucleotide. Alternatively, the sequences encoding EGPCR, or any fragments thereof, may be cloned into a vector for the production of an mRNA probe. Such vectors are known in the art, are commercially available, and may be used to synthesize RNA probes in vitro by addition of an appropriate RNA polymerase such as T17, T3, or SP6 and labeled nucleotides. These procedures may be conducted using a variety of commercially available kits, such as those provided by Pharmacia Biotech Ltd., Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding EGPCR may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode EGPCR may be designed to contain signal sequences which direct secretion of EGPCR through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC, Manassas, Va.) and may be chosen to ensure the correct modification and processing of the foreign protein.

In another embodiment of the invention, natural, modified, or recombinant nucleic acid sequences encoding EGPCR may be ligated to a heterologous sequence resulting in translation of a fusion protein in any of the aforementioned host systems. For example, a chimeric EGPCR protein containing a heterologous moiety that can be recognized by a commercially available antibody may facilitate the screening of peptide libraries for inhibitors of EGPCR activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the EGPCR encoding sequence and the heterologous protein sequence, so that EGPCR may be cleaved away from the heterologous moiety following purification. Methods for fusion protein expression and purification are discussed in Ausubel (supra). A variety of commercially available kits may also be used to facilitate expression and purification of fusion proteins.

In a further embodiment of the invention, synthesis of radiolabeled EGPCR may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of EGPCR may be produced not only by recombinant production, but also by direct peptide synthesis using solid-phase techniques (Creighton, supra pp. 55–60). Protein synthesis may be performed by manual techniques or by automation. Automated synthesis may be achieved, for example, using the ABI 431A peptide synthesizer (Perkin Elmer). Various fragments of EGPCR may be synthesized separately and then combined to produce the full length molecule.

THERAPEUTICS

Chemical and structural similarity, in the context of sequences and motifs, exists among EGPCR and human Emr1 (GI 784994; SEQ ID NO:3) and human orphan Emr1-like GPCR (GI 2935597; SEQ ID NO:4). In addition, EGPCR is expressed in spleen, peripheral blood leukocytes, and bone marrow. Therefore, EGPCR appears to play a role in respiratory, inflammatory, and immunological disorders.

Therefore, in one embodiment, EGPCR or a fragment or derivative thereof may be administered to a subject to treat or prevent a disorder associated with decreased expression or activity of EGPCR. Such disorders can include, but are not limited to, a respiratory disorder, such as, allergies, asthma, acute inflammatory lung disease, chronic inflammatory lung disease, chronic obstructive pulmonary dysplasia, emphysema, adult respiratory distress syndrome, bronchitis, and intestitial lung diseases; complications of cancer, hemodialysis, and extracorporeal circulation, viral, bacterial, fungal, parasitic, protozoal, and helminthic infections, and trauma; an inflammatory disorder, such as, rheumatoid arthritis, osteoarthritis, inflammatory bowel disease, adult respiratory distress syndrome, allergies, asthma, bronchitis, cholecystitis, contact dermatitis, Crohn's disease, atopic dermatitis, emphysema, episodic lymphopenia with lymphocytotoxins, erythroblastosis fetal is, erythema nodosum, atrophic gastritis, glomerulonephritis, Goodpasture's syndrome, gout, Graves' disease, Hashimoto's thyroiditis, hypereosinophilia, intestitial lung disease, myasthenia gravis, myocardial or pericardial inflammation, pancreatitis, polymyositis, psoriasis, Reiter's syndrome, scleroderma, Sjögren's syndrome, systemic anaphylaxis, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; and an immunological disorder, such as, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.

In another embodiment, a vector capable of expressing EGPCR or a fragment or derivative thereof may be administered to a subject to treat or prevent a disorder associated with decreased expression or activity of EGPCR including, but not limited to, those described above.

In a further embodiment, a pharmaceutical composition comprising a substantially purified EGPCR in conjunction with a suitable pharmaceutical carrier may be administered to a subject to treat or prevent a disorder associated with decreased expression or activity of EGPCR including, but not limited to, those provided above.

In still another embodiment, an agonist which modulates the activity of EGPCR may be administered to a subject to treat or prevent a disorder associated with decreased expression or activity of EGPCR including, but not limited to, those listed above.

In a further embodiment, an antagonist of EGPCR may be administered to a subject to treat or prevent a disorder associated with increased expression or activity of EGPCR. Such a disorder may include, but is not limited to, those respiratory, inflammatory, and immunological disorders discussed above. In one aspect, an antibody which specifically binds EGPCR may be used directly as an antagonist or indirectly as a targeting or delivery mechanism for bringing a pharmaceutical agent to cells or tissue which express EGPCR.

In an additional embodiment, a vector expressing the complement of the polynucleotide encoding EGPCR may be administered to a subject to treat or prevent a disorder associated with increased expression or activity of EGPCR including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of EGPCR may be produced using methods which are generally known in the art. In particular, purified EGPCR may be used to produce antibodies or to screen libraries of pharmaceutical agents to identify those which specifically bind EGPCR. Antibodies to EGPCR may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of polyclonal antibodies, various hosts including goats, rabbits, rats, mice, humans, and others may be immunized by injection with EGPCR or with any fragment or oligopeptide thereof which has immunogenic properties. Rats and mice are preferred hosts for downstream applications involving monoclonal antibody production. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable. The methods for antibody production and analysis are described in Harlow, E. and Lane, D. (1988; *Antibodies: A Laboratory Manual*, Cold Spring Harbor Laboratory, Cold Spring Harbor, N.Y.).

It is preferred that the oligopeptides, peptides, or fragments used to induce antibodies to EGPCR have an amino acid sequence consisting of at least about 5 amino acids, and, more preferably, of at least about 14 amino acids. It is also preferable that these oligopeptides, peptides, or fragments are identical to a portion of the amino acid sequence of the natural protein and contain the entire amino acid sequence of a small, naturally occurring molecule. Short stretches of EGPCR amino acids may be fused with those of another protein, such as KLH, and antibodies to the chimeric molecule may be produced.

Monoclonal antibodies to EGPCR may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120, respectively).

In addition, techniques developed for the production of "chimeric antibodies," such as the splicing of mouse antibody genes to human antibody genes to obtain a molecule with appropriate antigen specificity and biological activity, can be used (Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454). Alternatively, techniques described for the production of single chain antibodies may be adapted, using methods known in the art, to produce EGPCR-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:10134–10137).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for EGPCR may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 246:1275–1281).

Various immunoassays may be used for screening to identify antibodies having the desired specificity and minimal cross-reactivity. Numerous protocols for competitive binding or immunoradiometric assays using either polyclonal or monoclonal antibodies with established specificities are well known in the art. Such immunoassays typically involve the measurement of complex formation between EGPCR and its specific antibody. A two-site, monoclonal-based immunoassay utilizing monoclonal antibodies reactive to two non-interfering EGPCR epitopes is preferred, but a competitive binding assay may also be employed (Maddox, supra).

Various methods such as Scatchard analysis in conjunction with radioimmunoassay techniques may be used to assess the affinity of antibodies for EGPCR. Affinity is expressed as an association constant, $K_a$, which is defined as the molar concentration of EGPCR-antibody complex divided by the molar concentrations of free antigen and free antibody under equilibrium conditions. The $K_a$ determined for a preparation of polyclonal antibodies, which are heterogeneous in their affinities for multiple EGPCR epitopes, represents the average affinity, or avidity, of the antibodies for EGPCR. The $K_a$ determined for a preparation of monoclonal antibodies, which are monospecific for a particular EGPCR epitope, represents a true measure of affinity. High-affinity antibody preparations with $K_a$ ranging from about $10^9$ to $10^{12}$ L/mole are preferred for use in immunoassays in which the EGPCR-antibody complex must withstand rigorous manipulations. Low-affinity antibody preparations with $K_a$ ranging from about $10^6$ to $10^7$ L/mole are preferred for use in immunopurification and similar procedures which ultimately require dissociation of EGPCR, preferably in active form, from the antibody (Catty, D. (1988) *Antibodies, Volume I: A Practical Approach*, IRL Press, Washington, D.C.; Liddell, J. E. and Cryer, A. (1991) *A Practical Guide to Monoclonal Antibodies*, John Wiley & Sons, New York, N.Y.).

The titre and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is preferred for use in procedures requiring precipitation of EGPCR-antibody complexes. Procedures for evaluating antibody specificity, titer, and avidity, and guidelines for antibody quality and usage in various applications, are generally available (Catty, supra; Coligan, supra).

In another embodiment of the invention, the polynucleotides encoding EGPCR, or any fragment or complement thereof, may be used for therapeutic purposes. In one aspect, the complement of the polynucleotide encoding EGPCR may be used in situations in which it would be desirable to block the transcription of the mRNA. In particular, cells may be transformed with sequences complementary to polynucleotides encoding EGPCR. Thus, complementary molecules or fragments may be used to modulate EGPCR activity, or to achieve regulation of gene function. Such technology is now well known in the art, and sense or antisense oligonucleotides or larger fragments can be designed from various locations along the coding or control regions of sequences encoding EGPCR.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding EGPCR (Ausubel, supra).

Genes encoding EGPCR can be turned off by transforming a cell or tissue with expression vectors which express high levels of a polynucleotide, or fragment thereof, encoding EGPCR. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding EGPCR. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) in Huber, B. E. and B. I. Carr, *Molecular and Immunologic Approaches*, Futura Publishing Co., Mt. Kisco, N.Y., pp. 163–177). A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding EGPCR.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding EGPCR. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art (Goldman, C. K. et al. (1997) Nature Biotechnology 15:462–466).

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of EGPCR, antibodies to EGPCR, and mimetics, agonists, antagonists, or inhibitors of EGPCR. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0. 1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of EGPCR, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example EGPCR or fragments thereof, antibodies of EGPCR, and agonists, antagonists or inhibitors of EGPCR, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind EGPCR may be used for the diagnosis of disorders characterized by expression of EGPCR, or in assays to monitor patients being treated with EGPCR or agonists, antagonists, or inhibitors of EGPCR. Antibodies useful for diagnostic purposes may be prepared in the same manner as described above for therapeutics. Diagnostic assays for EGPCR include methods which utilize the antibody and a label to detect EGPCR in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring EGPCR, including ELISAs, RIAs, and FACS, are known in the art and provide a basis for diagnosing altered or abnormal levels of EGPCR expression. Normal or standard values for EGPCR expression are established by combining body fluids or cell extracts taken from normal mammalian subjects, preferably human, with antibody to EGPCR under conditions suitable for complex formation The amount of standard complex formation may be quantitated by various methods, preferably by photometric means. Quantities of EGPCR expressed in subject, samples from biopsied tissues are compared with the standard values. Deviation between standard and subject values establishes the parameters for diagnosing disease.

In another embodiment of the invention, the polynucleotides encoding EGPCR may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of EGPCR may be correlated with disease. The diagnostic assay may be used to determine absence, presence, and excess expression of EGPCR, and to monitor regulation of EGPCR levels during therapeutic intervention.

In one aspect, hybridization with PCR probes which are capable of detecting polynucleotide sequences, including genomic sequences, encoding EGPCR or closely related molecules may be used to identify nucleic acid sequences which encode EGPCR. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding EGPCR, allelic variants, or related sequences.

Probes may also be used for the detection of related sequences, and should preferably have at least 50% sequence identity to any of the EGPCR encoding sequences. The hybridization probes of the subject invention may be DNA or RNA and may be derived from the sequence of SEQ ID NO:2 or from genomic sequences including promoters, enhancers, and introns of the EGPCR gene.

Means for producing specific hybridization probes for DNAs encoding EGPCR include the cloning of polynucleotide sequences encoding EGPCR or EGPCR derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding EGPCR may be used for the diagnosis of a disorder associated with expression of EGPCR. Examples of such a disorder include, but are not limited to, a respiratory disorder, such as, allergies, asthma, acute inflammatory lung disease, chronic inflammatory lung disease, chronic obstructive pulmonary dysplasia, emphysema, adult respiratory distress syndrome, bronchitis, and intestitial lung diseases; complications of cancer, hemodialysis, and extracorporeal circulation, viral, bacterial, fungal, parasitic, protozoal, and helminthic infections, and trauma; an inflammatory disorder, such as, rheumatoid arthritis, osteoarthritis, inflammatory bowel disease, adult respiratory distress syndrome, allergies, asthma, bronchitis, cholecystitis, contact dermatitis, Crohn's disease, atopic dermatitis, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, intestitial lung disease, myasthenia gravis, myocardial or pericardial inflammation, pancreatitis, polymyositis, psoriasis, Reiter's syndrome, scleroderma, Sjögren's syndrome, systemic anaphylaxis, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; and an immunological disorder, such as, acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma. The polynucleotide sequences encoding EGPCR may be used in Southern or Northern analysis, dot blot, or other membrane-based technologies; in PCR technologies; in dipstick, pin, and ELISA assays; and in microarrays utilizing fluids or tissues from patients to detect altered EGPCR expression. Such qualitative or quantitative methods are well known in the art.

In a particular aspect, the nucleotide sequences encoding EGPCR may be useful in assays that detect the presence of associated disorders, particularly those mentioned above. The nucleotide sequences encoding EGPCR may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding EGPCR in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of EGPCR, a normal or standard profile for expression is established. This may be accomplished by combining body fluids or cell extracts taken from normal subjects, either animal or human, with a sequence, or a fragment thereof, encoding EGPCR, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcription biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding EGPCR may involve the use of PCR. These oligomers may be chemically synthesized, generated enzymatically, or produced in vitro. Oligomers will preferably contain a fragment of a polynucleotide encoding EGPCR, or a fragment of a polynucleotide complementary to the polynucleotide encoding EGPCR, and will be employed under optimized conditions for identification of a specific gene or condition. Oligomers may also be employed under less stringent conditions for detection or quantitation of closely related DNA or RNA sequences.

Methods which may also be used to quantitate the expression of EGPCR include radiolabeling or biotinylating nucleotides, coamplification of a control nucleic acid, and interpolating results from standard curves (Melby, P. C. et al. (1993) J. Immunol. Methods 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. See, for example, Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.

In another embodiment of the invention, nucleic acid sequences encoding EGPCR may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries (Price, C. M. (1993) Blood Rev. 7:127–134; Trask, B. J. (1991) Trends Genet. 7:149–154).

Fluorescent in situ hybridization (FISH) may be correlated with other physical chromosome mapping techniques and genetic map data (Heinz-Ulrich, et al. (1995) in Meyers, R. A. (ed.) *Molecular Biology and Biotechnology*, VCH Publishers New York, N.Y., pp. 965–968). Examples of genetic map data can be found in various scientific journals or at the Online Mendelian Inheritance in Man (OMIM) site. Correlation between the location of the gene encoding EGPCR on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation (Gatti, R. A. et al. (1988) Nature 336:577–580). The nucleotide sequence of the subject invention may also be used to detect differences in the chromosomal location due to translocation, inversion, etc., among normal, carrier, or affected individuals.

In another embodiment of the invention, EGPCR, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between EGPCR and the agent being tested may be measured.

Another technique for drug screening provides for high throughput screening of compounds having suitable binding affinity to the protein of interest (Geysen, et al. (1984) PCT application WO84/03564). In this method, large numbers of different small test compounds are synthesized on a solid substrate, such as plastic pins or some other surface. The test compounds are reacted with EGPCR, or fragments thereof, and washed. Bound EGPCR is then detected by methods well known in the art. Purified EGPCR can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding EGPCR specifically compete with a test compound for binding EGPCR. In this manier, antibodies can be used to detect the presence of any peptide which shares one or more antigenic determinants with EGPCR.

In additional embodiments, the nucleotide sequences which encode EGPCR may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. EOSINOT03 cDNA Library Construction

The eosinophils for the EOSINOT03 cDNA library were isolated from 200 to 400 ml of peripheral blood drawn from six allergic asthmatic donors, five of whom were male. The donors ranged in age from 31 to 42 and were allergic to common allergens such as dust, mold, pollen, animals, and, in one case, penicillin and some foods. Donors were medication-free for at least one week prior to blood donation. The whole blood samples were diluted 1:2 with cold 1×PIPES/glucose buffer, and each 25 ml of blood was layered onto a 15 ml cushion of 60% Percoll® (Sigma Aldrich, St. Louis, Mo.; 144 ml Percoll®/72 ml $H_2O$/24 ml 10×PIPES) in a 50 ml conical tube (on ice). The tubes were centrifuged at 2000 rpm at 4° C. for 35 minutes to separate mononuclear cells from granulocytes and red blood cells (RBCs). The serum, mononuclear cells and Percoll were aspirated, and the sides of the each tube were wiped with a cotton swab. Following hypotonic shock and differential centriftigation to remove RBC ghosts, eosinophils were separated from neutrophils by negative selection with magnetic anti-CD16 beads (Miltenyi Biotechnology, Auburn, Calif.). All eosinophil preparations were >98% pure.

Pooled eosinophils were centrifuged at 1000 rpm at room temperature for 5 minutes and then placed on ice. The supernatant was removed, and the cell pellet was washed once with phosphate buffered saline and then dissolved in 5 ml of buffer consisting of 5 M guanidine isothiocyanate, 10 mM EDTA, 50 mM Tris-HCl (pH 7.5) and 8% β-mercaptoethanol. A five-fold volume of 4 M LiCl was added to the buffer, and the mixture was stored in the refrigerator for more than sixteen hours. After centrifugation, the precipitate was washed once with 3 M LiCl and centrifuged once more. The second precipitate was dissolved in a solution of 0.1% sodium dodecyl sulfate, 1 mM EDTA, and 10 mM Tris-HCl (pH 7.5). The suspension was frozen at −70° C. and then vortexed during thawing.

Total RNA was extracted twice with phenol chloroform, once with chloroform, and precipitated with ethanol. Following centrifugation, the RNA pellet was redissolved in DEPC-treated, distilled deionized water (DEPC-dd$H_2$O) and pelleted through a CsCl gradient. The RNA was extracted with acid phenol (1×, pH 4.0, Ambion, Austin, Tex.), precipitated with ethanol and resuspended in DEPC-dd$H_2$O. The RNA was treated with RNAse-free DNAse (Epicentre Technologies, Madison, Wis.) for 15 minutes, extracted with chloroform, precipitated, washed with ethanol, and dissolved in DEPC-dd$H_2$O.

The mRNA was handled according to the recommended protocols in the SUPERSCRIPT plasmid system (Life Technologies). cDNA synthesis was initiated with a Not I-oligo d(T) primer. Double stranded cDNA was blunted, ligated to Sal I adaptors, digested with Not I, fractionated on a SEPHAROSE CL4B column (Amersham Pharmacia Biotech Ltd.), and those cDNAs exceeding 400 bp were ligated into the Not I and Sal I sites of the pSPORT vector (Life Technologies).

II Isolation and Sequencing of cDNA Clones

Plasmid DNA was released from the cells and purified using the R.E.A.L. PREP 96 plasmid kit (QIAGEN, Inc., Valencia, Calif.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Life Technologies) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

EGPCR was identified in Incyte Clone 429905 from the EOSINOT03 cDNA library. The cDNA of Incyte Clone 429905 was sequenced by in vitro transposon insertion using the Primer Island Transposon kit (PE Applied Biosystems, Foster City, Calif.). Briefly, the cDNA clone with ~3.5 kb insert was mixed and incubated with transposition reagents which contained the artificial AT2 transposon provided in the kit for one hour at 30° C. The transposition reagents contained the artificial AT2 transposon. The DNA mixture was electroporated into DH10B competent *E. coli* cells (Life Technologies) and plated onto LB agar plates containing ampicillin for plasmid selection and trimethoprim/chloramphenicol for transposon selection. Resistant colonies were mapped for transposon insertion site by PCR analysis, and DNA of clones with transposon insertion at various locations throughout the insert were sequenced with an ABI sequencer by the method of Sanger, F. and A. R. Coulson (1975; J. Mol. Biol. 94:441 f) . DNA sequences were assembled using the Autoassembler program (PE Applied Biosystems, Foster City, Calif.), and edited manually. The complete sequence was compiled from data of both DNA strands, and the reading frame was determined.

III. Analysis of cDNAs and Their Deduced Proteins

The polynucleotide sequences derived from cDNA sequencing were analyzed using a combination of software programs which utilize algorithms well known to those skilled in the art. Table 2 summarizes the software programs/ algorithms, descriptions of the programs, references, and threshold parameters used to identify and analyze EGPCR. The references cited in the third column of Table 2 are incorporated by reference herein. Sequences were also analyzed using MACDNASIS PRO software (Hitachi Software Engineering) and LASERGENE software (DNASTAR Inc, Madison, Wis.).

The cDNA sequences were validated by removing vector, linker, and poly A sequences and by masking ambiguous bases, using algorithms and programs based on BLAST, dynamic programing, and dinucleotide nearest neighbor analysis. The sequences were then queried against a selection of public databases such as GenBank primate, rodent, mammalian, vertebrate, and eukaryote databases to acquire annotation. Full length polynucleotide and amino acid sequences were analyzed by querying against databases such as the GenBank databases (described above), SwissProt, BLOCKS, PRINTS, PFAM, and PROSITE.

IV. Synthesis of EGPCR Probe and Northern Analysis

Membrane-based northern analysis was performed on 2 μg of poly A+RNA samples from a variety of human tissues on the multiple tissue northern blots (MTN, Clontech). Two DNA fragments were isolated from the EGPCR cDNA clone, a 539 bp Xba I-BamH I fragment and a 984 bp BamH I-EcoR I fragment. The fragments corresponded to most of the coding region between amino acid residues 173–353. The fragments were labeled with $^{33}$P isotope using the random primer DNA labeling method (High Primer DNA Labeling kit; Boehringer-Mannheim, Indianapolis, Ind.). Hybridization of the probe to the MTN blot was under conditions of high stringency (5× SSC, 50 mM NaPO$_4$, pH 7.4, 1× Denhardts, 2% SDS and 100 μg/ml salmon sperm DNA) at 65° C. for more than sixteen hours. The blots were washed with 2× SSC at room temperature two to three times, followed one or two washes with 0.2× SSC, 0.1% SDS at 50° C., and autoradiographed at –80° C.

Analogous computer techniques applying BLAST were used to search for identical or related molecules in the LIFESEQ database (Incyte Pharmaceuticals).

The basis of the search was the product score which is defined as:

% sequence identity×% maximum BLAST score/100

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of Northern analysis were reported as a list of libraries in which the transcript encoding EGPCR occurred. Electronic northern analysis involved the grouping of cDNA libraries into organ/tissue and disease categories. The organ/tissue categories were cardiovascular, dermatologic, developmental, endocrine, gastrointestinal, hematopoietic/immune, musculoskeletal, nervous, reproductive, and urologic, and the disease categories were cancer, inflammation/trauma, fetal, neurological, and pooled. The libraries in each category which expressed the sequence were counted, and the fraction of the total was caculated. The results of electronic Northern analysis were reported as the percentage distribution. Table 1 shows the results of electronic Northern analysis.

V. Labeling and Use of Individual Hybridization Probes

Hybridization probes derived from SEQ ID NO:2 were used to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, $^{250}$μCi of [γ-$^{32}$P] adenosine triphosphate (Amersham Pharmacia Biotech Ltd.), and T4 polynucleotide kinase (DuPont NEN, Boston, Mass.). The labeled oligonucleotides are substantially purified using a SEPHADEX G-25 superfine size exclusion dextran bead column (Amersham Pharmacia Biotech Ltd.). An aliquot containing 10$^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN).

The DNA from each digest is fractionated on a 0.7% agarose gel and transferred to nylon membranes (NYTRAN PLUS, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots, hybridization patterns are compared visually.

VI. Microarrays

A chemical coupling procedure and an ink jet device can be used to synthesize array elements on the surface of a substrate (Baldeschweiler, supra). An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate. The cDNA is fixed to the slide using UV cross-linking followed by thermal and chemical treatments and subsequently dried (cf. Schena, M. et al. (1995) Science 270:467–470; Shalon, D. et al. (1996) Genome Res. 6:639–645). Fluorescent probes are prepared and used for hybridization to the elements on the substrate. The substrate is analyzed by procedures described above.

VII. Complementary Polynucleotides

Sequences complementary to the EGPCR-encoding sequences, or any parts thereof, are used to detect, decrease, or inhibit expression of naturally occurring EGPCR. Although use of oligonucleotides comprising from about 15 to 30 base pairs is described, essentially the same procedure is used with smaller or with larger sequence fragments. Appropriate oligonucleotides are designed using OLIGO 4.06 software and the coding sequence of EGPCR. To inhibit transcription, a complementary oligonucleotide is designed from the most unique 5' sequence and used to prevent promoter binding to the coding sequence. To inhibit translation, a complementary oligonucleotide is designed to prevent ribosomal binding to the EGPCR-encoding transcript.

VIII. Expression of Recombinant EGPCR Protein

Expression of EGPCR was demonstrated by subcloning the cDNAs with or without an amino terminal Myc-tag into appropriate vectors and introducing the constructs into mammalian host cells, for example, HEK 293. A 539 bp Xba I—BamH I fragment and a 984 bp BamH I—EcoR I fragment of SEQ ID NO:2 containing the entire coding region was subcloned into a bi-cistronic green fluorescent protein (GFP) expression vector (CIEN.A12, Pfizer Inc., Groton, Conn.). The vector links the expression of the inserted cDNA with that of GFP via an internal ribosomal entry site (IRES). Thus the inserted cDNA and GFP are cotranscribed as a single messenger RNA molecule but are translated separately. The expression of GFP indicates transcription of the inserted cDNA. A Myc tag was engineered in front of the amino terminus of EGPCR using PCR method with primers containing Myc tag sequence joined with EGPCR-specific sequence to detect EGPCR expression in transfected cells.

Expression constructs were transfected into HEK 293 cells (Kelly Mayo, Department of Biochemistry, Northwest University, Chicago, Ill.) using LipofectAMINE reagent (Life Technologies). Stable cell lines were obtained by cotransfection with a vector containing a hygromycin resistance gene, and transfected cells were cultured in the presence of 5 µg/ml hygromycin. Transfected cells expressing GFP were further enriched by FACS sorting.

IX. Demonstration of EGPCR Activity

EGPCR, or biologically active fragments thereof, are labeled with $^{125}$I Bolton-Hunter reagent (Bolton et al. (1973) Biochem. J. 133:529). Candidate molecules previously arrayed in the wells of a multi-well plate are incubated with the labeled EGPCR, washed, and any wells with labeled EGPCR complex are assayed. Data obtained using different concentrations of EGPCR are used to calculate values for the number, affinity, and association of EGPCR with the candidate molecules.

X. Functional Assays

EGPCR function is assessed by expressing the sequences encoding EGPCR at physiologically elevated levels in mammalian cell culture systems. cDNA is subcloned into a mammalian expression vector containing a strong promoter that drives high levels of cDNA expression. Vectors of choice include pCMV SPORT (Life Technologies) and pCR 3.1 (Invitrogen, Carlsbad, Calif.), both of which contain the cytomegalovirtis promoter. 5–10 µg of recombinant vector are transiently transfected into a human cell line, preferably of endothelial or hematopoietic origin, using either liposome formulations or electroporation. 1–2 µg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; downregulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994; Flow Cytometry, Oxford, New York, N.Y.).

The influence of EGPCR on gene expression can be assessed using highly purified populations of cells transfected with sequences encoding EGPCR and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding EGPCR and other genes of interest can be analyzed by Northern analysis or microarray techniques.

XI. Production of EGPCR Specific Antibodies

An oligopeptide of 10 amino acid residues (equivalent to residues 121 to 130 of full-length EGPCR) located within the extracellular region of EGPCR was synthesized using methods well-known in the art. Two rabbits were immunized with the oligopeptide-KLH complex in complete Freund's adjuvant (Charles River, Wilmington, Mass.) using methods well-known in the art. The resulting antisera, R5833, was tested for antipeptide activity by ELISA. R5833 antiserum recognized recombinant protein expressed in mammalian HEK 293 cells by Western blot analysis.

XII. Western Blot Analyses and Deglycosylation

Transfected HEK 293 cells containing the EGPCR expression constructs (429905-GFP and Myc-429905-GFP) were lysed with buffer containing 25 mM Tris-HCl, pH 7.4, 1 mM MgCl$_2$, 100 mM NaCl, 2 mM EDTA, 1% Triton X-100, 4 mM Pefabloc (Boehringer Mannheim) and sonicated with microtips (70% duty power) using two to three pulses. Proteins were separated on a denaturing polyacrylamide gel (NuPage gels, Novex, San Diego, Calif.) and transferred onto a nitrocellulose membrane as described in Ausubel (supra). The blot was then probed with antiserum R5833 in buffer, and washed. The blot was then incubated with a secondary antibody, HRP (horseradish peroxidase)-conjugated donkey anti-rabbit Ig, and visualized using ECL (enhanced chemiluminescence) system (Amersham Pharmacia Biotech Ltd.).

Total cell membranes were isolated by suspension of cell pellets in ice-cold sucrose buffer (0.25 M sucrose, 0.1 M KPO$_4$, pH 7.4, 0.1 mM EDTA) and 4 mM Pefabloc, sonicated two to three times with microtips (70% duty power), and centrifuged at 100,000×g for 1 hour at 4° C. The S100 supernatant fraction was transferred to a fresh tube, the residual pellet was homogenized in ice cold "PEG" buffer (0.1 M KPO$_4$, pH 7.4, 0.1 mM EDTA, 20% glycerol). Deglycosylation was conducted using N-glycosidase F deglycosylation kit (Boehringer-Mannheim) following the manufacturer's instructions. The glycoprotein samples were heated at 95° C. for three minutes in denaturation buffer with 1% β-mercaptoethanol (v/v), reconstituted in buffer containing N-glycosidase, and incubated for 1 hour at 37° C. The reaction was stopped by addition of SDS-sample buffer and heating at 95° C. for three minutes.

XIII. Purification of Naturally Occurring EGPCR Using Specific Antibodies

Naturally occurring or recombinant EGPCR is substantially purified by immunoaffinity chromatography using antibodies specific for EGPCR. An immunoaffinity column is constructed by covalently coupling anti-EGPCR antibody to an activated chromatographic resin, such as CNBr-activated SEPHAROSE (Amersham Pharmacia Biotech Ltd.). After the coupling, the resin is blocked and washed according to the manufacturer's instructions.

Media containing EGPCR are passed over the immunoaffinity column, and the column is washed under conditions that allow the preferential absorbance of EGPCR (e.g., high ionic strength buffers in the presence of detergent). The column is eluted under conditions that disrupt antibody/EGPCR binding (e.g., a buffer of pH 2 to pH 3, or a high concentration of a chaotrope, such as urea or thiocyanate ion), and EGPCR is collected.

XIV. Demonstration of EGPCR Expression in Cells

Expression of EGPCR on the surface of transfected HEK 293 cells was demonstrated by immunofluorescent antibody staining followed by flow cytometry. Briefly, a Myc-tag was fused to the amino terminus of EGPCR immediately after the signal peptide in the bi-cistronic expression vector. The Myc-tagged EF-GFP cDNA construct (Myc-429905-GFP) or the control vector (GFP Control) was transfected into HEK 293 cells. Cells were stained first with murine anti-Myc antibody (Clone 9E10, Boehringer-Mannheim) or control murine immunoglobulin (PharMingen, San Diego, Calif.), and then with phycoerythrin (PE)-conjugated anti-mouse Ig (PharMingen). The cells were analyzed for GFP fluorescence intensity and phycoerythrin intensity on a FACSort flow cytometer (Becton Dickinson, San Diego, Calif.). Anti-Myc antibody stained Myc-tagged EF-GFP cDNA construct (Myc-429905-GFP) transfectants positively and failed to stain cells transfected with control vector. Cell surface expression was also demonstrated by fluorescence microscopy of HEK 293 transfectants expressing Myc-tagged EGPCR.

XV. Flow Cytometry and Immunofluorescence Staining

Cells were harvested and stained with a mouse anti-Myc antibody (Clone 9E10, Boehringer Mannheim) or isotype matched control mouse IgG (Pharmingen) at 4° C. for 30 minutes, washed, and then incubated with phycoerythrin (PE)-conjugated anti-mouse Ig (Pharmingen). The cells were then analyzed for GFP fluorescence intensity and phycoerythrin intensity on a FACSORT flow cytometer (Becton Dickinson). Transfected cells were maintained in tissue culture flasks and incubated with primary and secondary antibodies at 37° C. for 30 minutes and washed as described above. Immunofluorescence of the cells were visualized immediately with an epifluorescent microscope (Nikon, Tokyo, Japan).

XVI. Identification of Molecules Which Interact with EGPCR

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| SEQ ID NO | Tissue Expression | Disease Class |
|---|---|---|
| 1 | Hematopoietic/Immune (0.409) Cardiovascular (0.167) Reproductive (0.129) | Inflammation/Trauma (0.447) Cancer (0.227) |

TABLE 2

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch <50% |
| ABI AutoAssembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215: 403–410; Altschul, S. F. et al. (1997) Nucleic Acids Res. 25: 3389–3402. | ESTs: Probability value = 1.0E–8 or less Full Length sequences: Probability value = 1.0E–10 or less |
| FASTA | A Pearson and Lipman algorithm that serachs for similarity between a query sequence and a group of sequences of the same type. FASTA comprises as least functions: fasta, tfast, fastx, tfastx, and ssearch. | Pearson, W. R. and D. J. Lipman (1988) Proc. Natl. Acad Sci. 85: 2444–2448; Pearson, W. R. (1990) Methods Enzymol. 183: 63–98; and Smith, T. F. and M. S. Waterman (1981) Adv. Appl. Math. 2: 482–489. | ESTs: fast E value = 1.06E–6 Assembled ESTs: fasta Identity =95% or greater and Match length = 200 bases or greater; fastx E value = 1.0E–8 or less Full Length sequences = fastx score = 100 or greater |
| BLIMPS | A BLocks IMProved Searcher that matches a sequence against those in BLOCKS and PRINTS databases to for gene families, sequence homology, and structural fingerprint regions. | Henikoff, S and J. G. Henikoff, Nucl. Acid Res., 19: 6565–72, 1991. J. G. Henikoff and S. Henikoff (1996) Methods Enzymol. 266:88–105; and Attwood, T.K. et al. (1997) J. Chem. Inf. Comput. Sci. 37: 417–424. | Score = 1000 or greater; ratio of Score/Strength =0.75 or larger; and Probability value = 1.0E–3 or less |
| PFAM | A Hidden Markov Models-based application useful for protein family search. | Krogh, A. et al. (1994) J. Mol. Biol., 235: 1501–1531; Sonnhammer, E. L. L. et al. (1988) Nucleic Acids Res. 26: 320–322. | Score = 10–50 bits, depending on individual protein families |
| ProfileScan | An alogrithm that searches for structural and sequence motifs in protei sequences that match sequence patterns defined in Prosite. | Gribskov, M. et al. (1988) CABIOS 4: 61–66; Gribskov, et al, (1989) Methods Enzymol. 183: 146–159; Bairoch, A. et al. (1997) | Score = 4.0 or greater |

TABLE 2-continued

| Program | Description | Reference | Parameter Threshold |
|---|---|---|---|
| Phred | A base-calling algorithm that examines automated sequencer traces with high sensitivity and probability. | Nucleic Acids Res. 25: 217–221 Ewing, B. et al, (1988) Genome Res. 8: 175–185; Ewing, B. and P. Green (1998) Genome Res. 8: 186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2: 482–489; Smith, T. F. and Waterman (1981) J. Mol. Biol. 147: 195–197; and Green, P., University of Washington, Seattle, WA. | Score = 120 or greater; Match length = 56 or greater |
| Consed | A graphical tool for viewing and editing Phrap assemblies | Gordon, D. et al. (1998) Genome Res. 8: 195–202. | |
| SPScan | A weight matrix analysis program that scans protein sequences for the presence of secretory signal peptides. | Nielson, H. et al. (1997) Protein Engineering 10: 1–6; Claverie, J. M. and S. Audic (1997) CABIOS 12: 431–439. | Score = 5 or greater |
| Motifs | A program that searches amino acid sequences for patterns that matched those defined in Prosite. | Bairoch et al. supra; Wisconsin Package Program Manual, verison 9, page M51–59, Genetics Computer Group, Madison, WI. | |

SEQUENCE LISTING

<160> NUMBER OF SEQ ID NOS: 4

<210> SEQ ID NO 1
<211> LENGTH: 652
<212> TYPE: PRT
<213> ORGANISM: HOMO SAPIENS
<220> FEATURE:
<223> OTHER INFORMATION: 429905, EOSINOT03

<400> SEQUENCE: 1

```
Met Gln Gly Pro Leu Leu Pro Gly Leu Cys Phe Leu Leu Ser Leu
 1               5                  10                  15

Phe Gly Ala Val Thr Gln Lys Thr Lys Thr Ser Cys Ala Lys Cys Pro
                20                  25                  30

Pro Asn Ala Ser Cys Val Asn Asn Thr His Cys Thr Cys Asn His Gly
                35                  40                  45

Tyr Thr Ser Gly Ser Gly Gln Lys Leu Phe Thr Phe Pro Leu Glu Thr
        50                  55                  60

Cys Asn Asp Ile Asn Glu Cys Thr Pro Pro Tyr Ser Val Tyr Cys Gly
65                  70                  75                  80

Phe Asn Ala Val Cys Tyr Asn Val Glu Gly Ser Phe Tyr Cys Gln Cys
                85                  90                  95

Val Pro Gly Tyr Arg Leu His Ser Gly Asn Glu Gln Phe Ser Asn Ser
                100                 105                 110

Asn Glu Asn Thr Cys Gln Asp Thr Thr Ser Ser Lys Thr Thr Gln Gly
            115                 120                 125

Arg Lys Glu Leu Gln Lys Ile Val Asp Lys Phe Glu Ser Leu Leu Thr
            130                 135                 140

Asn Gln Thr Leu Trp Arg Thr Glu Gly Arg Gln Glu Ile Ser Ser Thr
145                 150                 155                 160

Ala Thr Thr Ile Leu Arg Asp Val Glu Ser Lys Val Leu Glu Thr Ala
                165                 170                 175

Leu Lys Asp Pro Glu Gln Lys Val Leu Lys Ile Gln Asn Asp Ser Val
            180                 185                 190

Ala Ile Glu Thr Gln Ala Ile Thr Asp Asn Cys Ser Glu Glu Arg Lys
            195                 200                 205

Thr Phe Asn Leu Asn Val Gln Met Asn Ser Met Asp Ile Arg Cys Ser
```

```
            210                 215                 220
Asp Ile Ile Gln Gly Asp Thr Gln Gly Pro Ser Val Ile Ala Phe Ile
225                 230                 235                 240

Ser Tyr Ser Ser Leu Gly Asn Ile Ile Asn Ala Thr Phe Phe Glu Glu
                245                 250                 255

Met Asp Lys Lys Asp Gln Val Tyr Leu Asn Ser Gln Val Val Ser Ala
                260                 265                 270

Ala Ile Gly Pro Lys Arg Asn Val Ser Leu Ser Lys Ser Val Thr Leu
            275                 280                 285

Thr Phe Gln His Val Lys Met Thr Pro Ser Thr Lys Lys Val Phe Cys
        290                 295                 300

Val Tyr Trp Lys Ser Thr Gly Gln Gly Ser Gln Trp Ser Arg Asp Gly
305                 310                 315                 320

Cys Phe Leu Ile His Val Asn Lys Ser His Thr Met Cys Asn Cys Ser
                325                 330                 335

His Leu Ser Ser Phe Ala Val Leu Met Ala Leu Thr Ser Gln Glu Glu
                340                 345                 350

Asp Pro Val Leu Thr Val Ile Thr Tyr Val Gly Leu Ser Val Ser Leu
            355                 360                 365

Leu Cys Leu Leu Leu Ala Ala Leu Thr Phe Leu Leu Cys Lys Ala Ile
        370                 375                 380

Gln Asn Thr Ser Thr Ser Leu His Leu Gln Leu Ser Leu Cys Leu Phe
385                 390                 395                 400

Leu Ala His Leu Leu Phe Leu Val Gly Ile Asp Arg Thr Glu Pro Lys
                405                 410                 415

Val Leu Cys Ser Ile Ile Ala Gly Ala Leu His Tyr Leu Tyr Leu Ala
                420                 425                 430

Ala Phe Thr Trp Met Leu Leu Glu Gly Val His Leu Phe Leu Thr Ala
            435                 440                 445

Arg Asn Leu Thr Val Val Asn Tyr Ser Ser Ile Asn Arg Leu Met Lys
        450                 455                 460

Trp Ile Met Phe Pro Val Gly Tyr Gly Val Pro Ala Val Thr Val Ala
465                 470                 475                 480

Ile Ser Ala Ala Ser Trp Pro His Leu Tyr Gly Thr Ala Asp Arg Cys
                485                 490                 495

Trp Leu His Leu Asp Gln Gly Phe Met Trp Ser Phe Leu Gly Pro Val
                500                 505                 510

Cys Ala Ile Phe Ser Ala Asn Leu Val Leu Phe Ile Leu Val Phe Trp
            515                 520                 525

Ile Leu Lys Arg Lys Leu Ser Ser Leu Asn Ser Glu Val Ser Thr Ile
        530                 535                 540

Gln Asn Thr Arg Met Leu Ala Phe Lys Ala Thr Ala Gln Leu Phe Ile
545                 550                 555                 560

Leu Gly Cys Thr Trp Cys Leu Gly Leu Leu Gln Val Gly Pro Ala Ala
                565                 570                 575

Gln Val Met Ala Tyr Leu Phe Thr Ile Ile Asn Ser Leu Gln Gly Phe
                580                 585                 590

Phe Ile Phe Leu Val Tyr Cys Leu Leu Ser Gln Gln Val Gln Lys Gln
            595                 600                 605

Tyr Gln Lys Trp Phe Arg Glu Ile Val Lys Ser Lys Ser Glu Ser Glu
        610                 615                 620

Thr Tyr Thr Leu Ser Ser Lys Met Gly Pro Asp Ser Lys Pro Ser Glu
625                 630                 635                 640
```

Gly Asp Val Phe Pro Gly Gln Val Lys Arg Lys Tyr
                645                 650

<210> SEQ ID NO 2
<211> LENGTH: 3350
<212> TYPE: DNA
<213> ORGANISM: HOMO SAPIENS
<220> FEATURE:
<221> NAME/KEY: unsure
<222> LOCATION: (3293)...(3293)
<223> OTHER INFORMATION: a or g or c or t/u, unknown, or other
<223> OTHER INFORMATION: 429905, EOSINOT03

<400> SEQUENCE: 2

| | | | | | |
|---|---|---|---|---|---|
| gcgtgggata | cccgtaccac | agaaatgcag | ggaccattgc | ttcttccagg | cctctgcttt | 60 |
| ctgctgagcc | tctttggagc | tgtgactcag | aaaaccaaaa | cttcctgtgc | taagtgcccc | 120 |
| ccaaatgctt | cctgtgtcaa | taacactcac | tgcacctgca | accatggata | tacttctgga | 180 |
| tctgggcaga | aactattcac | attccccttg | agacatgta | acgacattaa | tgaatgtaca | 240 |
| ccaccctata | gtgtatattg | tggatttaac | gctgtatgtt | acaatgtcga | aggaagtttc | 300 |
| tactgtcaat | gtgtcccagg | atatagactg | cattctggga | atgaacaatt | cagtaattcc | 360 |
| aatgagaaca | cctgtcagga | caccacctcc | tcaaagacaa | cccagggcag | gaaagagctg | 420 |
| caaaagattg | tggacaaatt | tgagtcactt | ctcaccaatc | agactttatg | gagaacagaa | 480 |
| gggagacaag | aaatctcatc | cacagctacc | actattctcc | gggatgtgga | atcgaaagtt | 540 |
| ctagaaactg | ccttgaaaga | tccagaacaa | aaagtcctga | aatccaaaa | cgatagtgta | 600 |
| gctattgaaa | ctcaagcgat | tacagacaat | tgctctgaag | aaagaaagac | attcaacttg | 660 |
| aacgtccaaa | tgaactcaat | ggacatccgt | tgcagtgaca | tcatccaggg | agacacacaa | 720 |
| ggtcccagtg | tcattgcctt | tatctcatat | tcttctcttg | gaaacatcat | aaatgcaact | 780 |
| ttttttgaag | agatggataa | gaaagatcaa | gtgtatctga | actctcaggt | tgtgagtgct | 840 |
| gctattggac | ccaaaaggaa | cgtgtctctc | tccaagtctg | tgacgctgac | tttccagcac | 900 |
| gtgaagatga | cccccagtac | caaaaaggtc | ttctgtgtct | actggaagag | cacagggcag | 960 |
| ggcagccagt | ggtccaggga | tggctgcttc | ctgatacacg | tgaacaagag | tcacaccatg | 1020 |
| tgtaattgca | gtcacctgtc | cagcttcgct | gtcctgatgg | ccctgaccag | ccaggaggag | 1080 |
| gatcccgtgc | tgactgtcat | cacctacgtg | gggctgagcg | tctctctgct | gtgcctcctc | 1140 |
| ctggcggccc | tcacttttct | cctgtgtaaa | gccatccaga | acaccagcac | ctcactgcat | 1200 |
| ctgcagctct | cgctctgcct | cttcctggcc | cacctcctct | tcctcgtggg | gattgatcga | 1260 |
| actgaaccca | aggtgctgtg | ctccatcatc | gccggtgctt | tgcactatct | ctacctggcc | 1320 |
| gccttcacct | ggatgctgct | ggagggtgtg | cacctcttcc | tcactgcacg | gaacctgaca | 1380 |
| gtggtcaact | actcaagcat | caatagactc | atgaagtgga | tcatgttccc | agtcggctat | 1440 |
| ggcgttcccg | ctgtgactgt | ggccatttct | gcagcctcct | ggcctcacct | ttatggaact | 1500 |
| gctgatcgat | gctggctcca | cctggaccag | ggattcatgt | ggagtttcct | tggcccagtc | 1560 |
| tgtgccattt | tctctgcgaa | tttagtattg | tttatcttgg | tcttttggat | tttgaaaaga | 1620 |
| aaactttcct | ccctcaatag | tgaagtgtca | accatccaga | acacaaggat | gctggctttc | 1680 |
| aaagcaacag | ctcagctctt | catcctgggc | tgcacatggt | gtctgggctt | gctacaggtg | 1740 |
| ggtccagctg | cccaggtcat | ggcctacctc | ttcaccatca | tcaacagcct | ccaaggcttc | 1800 |
| ttcatcttct | tggtctactg | cctcctcagc | cagcaggtcc | agaaacaata | tcaaaagtgg | 1860 |
| tttagagaga | tcgtaaaatc | aaaatctgag | tctgagacat | acacactttc | cagcaagatg | 1920 |

-continued

```
ggtcctgact caaaacccag tgaggggggat gttttttccag dacaagtgaa gagaaaatat    1980
taaaactaga atattcaact ccatatggaa aatcatatcc atggatctct ttggcattat    2040
gaagaatgaa gctaaggaaa agggaattca ttaaacatat catccttgga gaggaagtaa    2100
tcaacccttta cttcccaaac tgtttgttct ccacaatagg ctctcaacaa atgtgtggta    2160
aattgcattt ctcttcacta tggtgtattc agtcaatgct tgtccctgga aacccaaagc    2220
atgaccactg caaatatttc cttgactttt tgtaaatgaa gaggtccttt tcctcaagtt    2280
cttagtccca ctcatcctaa acttgctctt tttttaagac agagtttcac tctgtcaccc    2340
aggctggagt gtagtggcat gatcgtagct cactgcagcc tcaaactcca gagctcaact    2400
ggttctccag cctcagcttc ccaaagtgct gggattacag gcatgagcca ctgcacctgg    2460
ccataaactt gctctttaaa ctcactcatt ccctcaaacc atcagcttcc tactggcttt    2520
acttccttgc tagatacagg ctaattttt tttttttttt tttttttttt tgagatggag    2580
tttcgctctt gttgcccagg ctggagtgca acggcgtgag tgcaacctct gcctcccggg    2640
ttcaagcgat tcttctgcct cagcctccca gtagctggc gttacaggta tggaccacca    2700
tgtccggcta attttgtatt tttagtagag acagggtttc tccatgttgg tcaggctggt    2760
ctcgaactcc cagcctcagg tgatccacct gacttggcct cccaagagtg ctgggattac    2820
aggcatgagc accgtgccc agcccaggct aacttatttt cttctgagac tgagtctcac    2880
tactgtcacc caggctggag tgcagtggtg agatctaggc tcactgcaac ctctacctcc    2940
tgggttcaag caattctcct gccttagcct cccgatagct gggactacaa gcacatgccg    3000
ccatgcccag ctaattttgt attttagtg gagacaaggt ttcaccatgt tggccaggct    3060
gatctcaaac tcctgacctc aagcagcgat ccacctgccg gggcctccca aagtgctggg    3120
attacagaca caagccatcg cgcctgatga gagattttaa gtgttctcac cacaaaaaaa    3180
aagaaaaaaa agtatatga ggtaatcgta tattaattag cttgacttag tcattccacg    3240
atgtagatat atttcaaaac atcctgttgt acatgataaa tatatatatt ttngtctata    3300
taaaacaaat aaataaataa atgtttaaag tgtaaaaaaa aaaaaaaag               3350
```

<210> SEQ ID NO 3
<211> LENGTH: 886
<212> TYPE: PRT
<213> ORGANISM: HOMO SAPIENS
<220> FEATURE:
<223> OTHER INFORMATION: 784994, GenBank

<400> SEQUENCE: 3

```
Met Arg Gly Phe Asn Leu Leu Phe Trp Gly Cys Cys Val Met His
 1               5                  10                  15

Ser Trp Glu Gly His Ile Arg Pro Thr Arg Lys Pro Asn Thr Lys Gly
                20                  25                  30

Asn Asn Cys Arg Asp Ser Thr Leu Cys Pro Ala Tyr Ala Thr Cys Thr
            35                  40                  45

Asn Thr Val Asp Ser Tyr Tyr Cys Thr Cys Lys Gln Gly Phe Leu Ser
        50                  55                  60

Ser Asn Gly Gln Asn His Phe Lys Asp Pro Gly Val Arg Cys Lys Asp
    65                  70                  75                  80

Ile Asp Glu Cys Ser Gln Ser Pro Gln Pro Cys Gly Pro Asn Ser Ser
                85                  90                  95

Cys Lys Asn Leu Ser Gly Arg Tyr Lys Cys Ser Cys Leu Asp Gly Phe
            100                 105                 110
```

-continued

```
Ser Ser Pro Thr Gly Asn Asp Trp Val Pro Gly Lys Pro Gly Asn Phe
    115                 120                 125

Ser Cys Thr Asp Ile Asn Glu Cys Leu Thr Ser Arg Val Cys Pro Glu
130                 135                 140

His Ser Asp Cys Val Asn Ser Met Gly Ser Tyr Ser Cys Ser Cys Gln
145                 150                 155                 160

Val Gly Phe Ile Ser Arg Asn Ser Thr Cys Glu Asp Val Asn Glu Cys
                165                 170                 175

Ala Asp Pro Arg Ala Cys Pro Glu His Ala Thr Cys Asn Asn Thr Val
            180                 185                 190

Gly Asn Tyr Ser Cys Phe Cys Asn Pro Gly Phe Glu Ser Ser Ser Gly
        195                 200                 205

His Leu Ser Cys Gln Gly Leu Lys Ala Ser Cys Glu Asp Ile Asp Glu
    210                 215                 220

Cys Thr Glu Met Cys Pro Ile Asn Ser Thr Cys Thr Asn Thr Pro Gly
225                 230                 235                 240

Ser Tyr Phe Cys Thr Cys His Pro Gly Phe Ala Pro Ser Ser Gly Gln
                245                 250                 255

Leu Asn Phe Thr Asp Gln Gly Val Glu Cys Arg Asp Ile Asp Glu Cys
            260                 265                 270

Arg Gln Asp Pro Ser Thr Cys Gly Pro Asn Ser Ile Cys Thr Asn Ala
        275                 280                 285

Leu Gly Ser Tyr Ser Cys Gly Cys Ile Val Gly Phe His Pro Asn Pro
    290                 295                 300

Glu Gly Ser Gln Lys Asp Gly Asn Phe Ser Cys Gln Arg Val Leu Phe
305                 310                 315                 320

Lys Cys Lys Glu Asp Val Ile Pro Asp Asn Lys Gln Ile Gln Gln Cys
                325                 330                 335

Gln Glu Gly Thr Ala Val Lys Pro Ala Tyr Val Ser Phe Cys Ala Gln
            340                 345                 350

Ile Asn Asn Ile Phe Ser Val Leu Asp Lys Val Cys Glu Asn Lys Thr
        355                 360                 365

Thr Val Val Ser Leu Lys Asn Thr Thr Glu Ser Phe Val Pro Val Leu
    370                 375                 380

Lys Gln Ile Ser Met Trp Thr Lys Phe Thr Lys Glu Glu Thr Ser Ser
385                 390                 395                 400

Leu Ala Thr Val Phe Leu Glu Ser Val Glu Ser Met Thr Leu Ala Ser
                405                 410                 415

Phe Trp Lys Pro Ser Ala Asn Val Thr Pro Ala Val Arg Ala Glu Tyr
            420                 425                 430

Leu Asp Ile Glu Ser Lys Val Ile Asn Lys Glu Cys Ser Glu Glu Asn
        435                 440                 445

Val Thr Leu Asp Leu Val Ala Lys Gly Asp Lys Met Lys Ile Gly Cys
    450                 455                 460

Ser Thr Ile Glu Glu Ser Glu Ser Thr Glu Thr Thr Gly Val Ala Phe
465                 470                 475                 480

Val Ser Phe Val Gly Met Glu Ser Val Leu Asn Glu Arg Phe Phe Gln
                485                 490                 495

Asp His Gln Ala Pro Leu Thr Thr Ser Glu Ile Lys Leu Lys Met Asn
            500                 505                 510

Ser Arg Val Val Gly Gly Ile Met Thr Gly Glu Lys Lys Asp Gly Phe
        515                 520                 525

Ser Asp Pro Ile Ile Tyr Thr Leu Glu Asn Val Gln Pro Lys Gln Lys
    530                 535                 540
```

| | | | | | | | | | | | | | | |
|---|---|---|---|---|---|---|---|---|---|---|---|---|---|---|
|Phe|Glu|Arg|Pro|Ile|Cys|Val|Ser|Trp|Ser|Thr|Asp|Val|Lys|Gly|Gly|
|545| | | | |550| | | | |555| | | | |560|

Arg Trp Thr Ser Phe Gly Cys Val Ile Leu Glu Ala Ser Glu Thr Tyr
 565 570 575

Thr Ile Cys Ser Cys Asn Gln Met Ala Asn Leu Ala Val Ile Met Ala
 580 585 590

Ser Gly Glu Leu Thr Met Asp Phe Ser Leu Tyr Ile Ile Ser His Val
 595 600 605

Gly Ile Ile Ile Ser Leu Val Cys Leu Val Leu Ala Ile Ala Thr Phe
 610 615 620

Leu Leu Cys Arg Ser Ile Arg Asn His Asn Thr Tyr Leu His Leu His
625 630 635 640

Leu Cys Val Cys Leu Leu Leu Ala Lys Thr Leu Phe Leu Ala Gly Ile
 645 650 655

His Lys Thr Asp Asn Lys Thr Gly Cys Ala Ile Ile Ala Gly Phe Leu
 660 665 670

His Tyr Leu Phe Leu Ala Cys Phe Phe Trp Met Leu Val Glu Ala Val
 675 680 685

Ile Leu Phe Leu Met Val Arg Asn Leu Lys Val Val Asn Tyr Phe Ser
 690 695 700

Ser Arg Asn Ile Lys Met Leu His Ile Cys Ala Phe Gly Tyr Gly Leu
705 710 715 720

Pro Met Leu Val Val Val Ile Ser Ala Ser Val Gln Pro Gln Gly Tyr
 725 730 735

Gly Met His Asn Arg Cys Trp Leu Asn Thr Glu Thr Gly Phe Ile Trp
 740 745 750

Ser Phe Leu Gly Pro Val Cys Thr Val Ile Val Ile Asn Ser Leu Leu
 755 760 765

Leu Thr Trp Thr Leu Trp Ile Leu Arg Gln Arg Leu Ser Ser Val Asn
 770 775 780

Ala Glu Val Ser Thr Leu Lys Asp Thr Arg Leu Leu Thr Phe Lys Ala
785 790 795 800

Phe Ala Gln Leu Phe Ile Leu Gly Cys Ser Trp Val Leu Gly Ile Phe
 805 810 815

Gln Ile Gly Pro Val Ala Gly Val Met Ala Tyr Leu Phe Thr Ile Ile
 820 825 830

Asn Ser Leu Gln Gly Ala Phe Ile Phe Leu Ile His Cys Leu Leu Asn
 835 840 845

Gly Gln Val Arg Glu Glu Tyr Lys Arg Trp Ile Thr Gly Lys Thr Lys
 850 855 860

Pro Ser Ser Gln Ser Gln Thr Ser Arg Ile Leu Leu Ser Ser Met Pro
865 870 875 880

Ser Ala Ser Lys Thr Gly
 885

SEQ ID NO 4
LENGTH: 344
TYPE: PRT
ORGANISM: HOMO SAPIENS
FEATURE:
OTHER INFORMATION: 2935597, GenBank

SEQUENCE: 4

Lys Val Leu Cys Val Phe Trp Glu His Gly Gln Asn Gly Cys Gly His
1 5 10 15

```
Trp Ala Thr Thr Gly Cys Ser Thr Ile Gly Thr Arg Asp Thr Ser Thr
            20              25              30
Ile Cys Arg Cys Thr His Leu Ser Ser Phe Ala Val Leu Met Ala His
            35              40              45
Tyr Asp Val Gln Glu Asp Pro Val Leu Thr Val Ile Thr Tyr Met Gly
 50              55              60
Leu Ser Val Ser Leu Leu Cys Leu Leu Leu Ala Ala Leu Thr Phe Leu
 65              70              75              80
Leu Cys Lys Ala Ile Gln Asn Thr Ser Thr Ser Leu His Leu Gln Leu
            85              90              95
Ser Leu Cys Leu Phe Leu Ala His Leu Leu Phe Leu Val Ala Ile Asp
            100             105             110
Gln Thr Gly His Lys Val Leu Cys Ser Ile Ile Ala Gly Thr Leu His
            115             120             125
Tyr Leu Tyr Leu Ala Thr Phe Thr Trp Met Leu Leu Glu Ala Leu Tyr
 130             135             140
Leu Phe Leu Thr Ala Arg Asn Leu Thr Val Val Asn Tyr Ser Ser Ile
 145             150             155             160
Asn Arg Phe Met Lys Lys Leu Met Phe Pro Val Gly Tyr Gly Val Pro
            165             170             175
Ala Val Thr Val Ala Ile Ser Ala Ala Ser Arg Pro His Leu Tyr Gly
            180             185             190
Thr Pro Ser Arg Cys Trp Leu Gln Pro Glu Lys Gly Phe Ile Trp Gly
            195             200             205
Phe Leu Gly Pro Val Cys Ala Ile Phe Ser Val Asn Leu Val Leu Phe
 210             215             220
Leu Val Thr Leu Trp Ile Leu Lys Asn Arg Leu Ser Ser Leu Asn Ser
225             230             235             240
Glu Val Ser Thr Leu Arg Asn Thr Arg Met Leu Ala Phe Lys Ala Thr
            245             250             255
Ala Gln Leu Phe Ile Leu Gly Cys Thr Trp Cys Leu Gly Ile Leu Gln
            260             265             270
Val Gly Pro Ala Ala Arg Val Met Ala Tyr Leu Phe Thr Ile Ile Asn
            275             280             285
Ser Leu Gln Gly Val Phe Ile Phe Leu Val Tyr Cys Leu Leu Ser Gln
            290             295             300
Gln Val Arg Glu Gln Tyr Gly Lys Trp Ser Lys Gly Ile Arg Lys Leu
305             310             315             320
Lys Thr Glu Ser Glu Met His Thr Leu Ser Ser Ser Ala Lys Ala Asp
            325             330             335
Thr Ser Lys Pro Ser Thr Val Asn
            340
```

We claim:

1. An isolated and purified polynucleotide fragment encoding the polypeptide of SEQ ID NO:1.

2. An isolated and purified polynucleotide which is completely complementary to the polynucleotide of SEQ ID NO:1.

3. An isolated and purified polynucleotide fragment comprising the polynucleotide sequence of SEQ ID NO:2.

4. An isolated and purified polynucleotide which is completely complementary to the polynucleotide of SEQ ID NO:2.

5. An expression vector comprising the polynucleotide fragment of claim 1.

6. A host cell comprising the expression vector of claim 5.

7. A method for producing a polypeptide comprising the sequence of SEQ ID NO:1, the method comprising the steps of:

a) culturing the host cell of claim 6 under conditions suitable for the expression of the polynucleotide; and b) recovering the polypeptide from the host cell culture.

* * * * *